(12) United States Patent
Gazit et al.

(10) Patent No.: US 12,070,746 B2
(45) Date of Patent: *Aug. 27, 2024

(54) METHOD OF OSTEOGENIC DIFFERENTIATION IN MICROFLUIDIC TISSUE CULTURE SYSTEMS

(71) Applicants: EMULATE, INC., Boston, MA (US); CEDARS-SINAI MEDICAL CENTER, Los Angeles, CA (US)

(72) Inventors: Dan Gazit, Los Angeles, CA (US); Gadi Pelled, Los Angeles, CA (US); Zulma Gazit, Los Angeles, CA (US); Dmitriy Sheyn, Los Angeles, CA (US); Christopher David Hinojosa, Cambridge, MA (US); Norman Wen, West Roxbury, MA (US); Geraldine Hamilton, Boston, MA (US)

(73) Assignees: EMULATE, Inc., Boston, MA (US); CEDARS-SINAI MEDICAL CENTER, Los Angeles, CA (US)

( * ) Notice: Subject to any disclaimer, the term of this patent is extended or adjusted under 35 U.S.C. 154(b) by 122 days.

This patent is subject to a terminal disclaimer.

(21) Appl. No.: 15/958,142

(22) Filed: Apr. 20, 2018

(65) Prior Publication Data

US 2018/0305668 A1 Oct. 25, 2018

Related U.S. Application Data

(63) Continuation-in-part of application No. PCT/US2017/013250, filed on Jan. 12, 2017.

(60) Provisional application No. 62/277,857, filed on Jan. 12, 2016.

(51) Int. Cl.
| | | |
|---|---|---|
| C12N 5/077 | (2010.01) |
| A61K 49/00 | (2006.01) |
| A61K 51/02 | (2006.01) |
| A61L 27/38 | (2006.01) |
| B01L 3/00 | (2006.01) |
| C12N 5/00 | (2006.01) |
| C12N 5/071 | (2010.01) |
| C12N 5/074 | (2010.01) |
| C12N 5/0775 | (2010.01) |
| G01N 33/50 | (2006.01) |
| G01T 1/164 | (2006.01) |
| G01T 1/29 | (2006.01) |
| C07K 14/78 | (2006.01) |
| C12M 1/34 | (2006.01) |

(52) U.S. Cl.
CPC ........ *B01L 3/5027* (2013.01); *A61K 49/0019* (2013.01); *A61K 49/005* (2013.01); *A61K 51/02* (2013.01); *A61L 27/3895* (2013.01); *B01L 3/5085* (2013.01); *C12N 5/0062* (2013.01); *C12N 5/0075* (2013.01); *C12N 5/0654* (2013.01); *C12N 5/0655* (2013.01); *C12N 5/0662* (2013.01); *C12N 5/0663* (2013.01); *C12N 5/0668* (2013.01); *C12N 5/0696* (2013.01); *C12N 5/0697* (2013.01); *G01N 33/5038* (2013.01); *G01T 1/1644* (2013.01); *G01T 1/2985* (2013.01); *A61M 2205/3334* (2013.01); *C07K 14/78* (2013.01); *C12M 41/40* (2013.01)

(58) Field of Classification Search
CPC .. C12N 5/0062; C12N 5/0654; C12N 5/0663; C12N 5/0668; C07K 14/78; A61L 27/3895

See application file for complete search history.

(56) References Cited

U.S. PATENT DOCUMENTS

| | | | |
|---|---|---|---|
| 5,585,089 A | 12/1996 | Queen et al. | 424/130.1 |
| 2007/0128722 A1* | 6/2007 | Lin | C12N 5/0663 |
| | | | 435/366 |
| 2009/0123383 A1 | 5/2009 | Frangioni | 424/9.6 |
| 2014/0186414 A1 | 7/2014 | Ingber et al. | 435/325 |
| 2014/0248621 A1 | 9/2014 | Collins | 435/173.9 |
| 2015/0151011 A1 | 6/2015 | Jang et al. | 530/329 |
| 2016/0201037 A1 | 7/2016 | Tuan et al. | 435/294.1 |

FOREIGN PATENT DOCUMENTS

| | | |
|---|---|---|
| WO | WO/2014/172682 | 10/1914 |
| WO | WO/2015/126528 | 8/1915 |
| WO | WO/2017/096297 | 6/2017 |

OTHER PUBLICATIONS

Kim et al. A practical guide to microfluidic perfusion culture of adherent mammalian cells. Lab Chip, 2007, 7, 681-694 (Year: 2007).*

(Continued)

*Primary Examiner* — Teresa E Knight
(74) *Attorney, Agent, or Firm* — Medlen & Carroll, LLP

(57) ABSTRACT

Microfluidic "organ-on-a-chip" devices have been developed with the aim to replicate human tissues in vitro. However, there is no option to quantitatively monitor biological processes that take place within the chip, over time. Destructive methods in order to analyze, tissue formation, gene expression, protein secretion etc. require the harvest of the "tissue" at a certain time point. Described herein are methods and compositions for non-destructive molecular imaging methods and systems in order to quantitatively monitor specific biological processes, over time, within the chip, without the need to harvest.

18 Claims, 22 Drawing Sheets

(56) References Cited

OTHER PUBLICATIONS

Maegawa et al. Enhancement of osteoblastic differentiation of mesenchymal stromal cells cultured by selective combination of bone morphogenetic protein-2 (BMP-2) and fibroblast growth factor-2 (FGF-2). J Tissue Eng Regen Med 2007; 1: 306-313 (Year: 2007).*
Kreke et al. Effect of Intermittent Shear Stress on Mechanotransductive Signaling and Osteoblastic Differentiation of Bone Marrow Stromal Cells. Tissue Engineering: Part A vol. 14, No. 4, 2008. p. 529-537 (Year: 2008).*
Bohrnsen et al. Supportive angiogenic and osteogenic differentiation of mesenchymal stromal cells and endothelial cells in monolayer and co-cultures. International Journal of Oral Science (2016) 8, 223-230 (Year: 2016).*
Nishimura et al. Effect of osteogenic differentiation medium on proliferation and differentiation of human mesenchymal stem cells in threedimensional culture with radial flow bioreactor. Regenerative Therapy 2 (2015) 24-31 (Year: 2015).*
Kim et al. Shear Stress Induced by an Interstitial Level of Slow Flow Increases the Osteogenic Differentiation of Mesenchymal Stem Cells through TAZ Activation. PLoS One 9(3): e92427. p. 1-9 (Year: 2014).*
Zhang. Regulation and patterning of cell differentiation and pluripotency. Thesis. Columbia University. p. 1-177 (Year: 2011).*
Gomes & Fernandes, "Effect of therapeutic levels of doxycycline and minocycline in the proliferation and differentiation of human bone marrow osteoblastic cells" (2007) Arch Oral Biol, vol. 52: 251-259. (Year: 2007).*
Allen, L. V. (2012) *Remington: The Science and Practice of Pharmacy, vol. I and vol. II. Twenty-second edition*, Pharmaceutical Press, Philadelphia, PA.
Anderson, D. E. et al. (2017) "Dynamic Mechanical Compression of Chondrocytes for Tissue Engineering: A Critical Review," *Frontiers in Bioengineering and Biotechnology* 5, 76.
Aslan, H. et al. (2006) "Nucleofection-Based Ex Vivo Nonviral Gene Delivery to Human Stem Cells as a Platform for Tissue Regeneration," *Tissue Engineering* 12(4), 877-889.
Ben Arav, A. et al. (2012) "Adeno-associated virus-coated allografts: a novel approach for cranioplasty," *Journal of Tissue Engineering and Regenerative Medicine* 6(10), e43-e50.
Benayahu, D. et al. (1989) "Bone marrow-derived stromal cell line expressing osteoblastic phenotype in vitro and osteogenic capacity in vivo," *Journal of Cellular Physiology* 140(1), 1-7.
Bergmann, S. et al. (2013) "The bioluminescent Listeria monocytogenes strain Xen32 is defective in flagella expression and highly attenuated in orally infected BALB/cJ mice," *Gut Pathogens* 5, 19-19.
Bhatia, S. N. et al. (2014) "Microfluidic organs-on-chips," *Nature Biotechnology* 32(8), 760-772.
Bhise, N. S. et al. (2014) "Organ-on-a-chip platforms for studying drug delivery systems," *Journal of Controlled Release* 190, 82-93.
Chang, J. et al. (2013) "NF-κB inhibits osteogenic differentiation of mesenchymal stem cells by promoting β-catenin degradation," *Proceedings of the National Academy of Sciences* 110(23), 9469.
Eagle, M. J. et al. (2015) "Production of an osteoinductive demineralised bone matrix powder without the use of organic solvents," *Cell and Tissue Banking* 16(3), 433-441.
Esch, E. W. et al. (2015) "Organs-on-chips at the frontiers of drug discovery," *Nature Reviews Drug Discovery* 14, 248.
Gomes, M. E. et al. (2017) "Tissue Engineering and Regenerative Medicine: New Trends and Directions—A Year in Review," *Tissue Engineering, Part B: Reviews* 23(3), 211-224.
Green, M. R. et al. (2012) *Molecular cloning: a laboratory manual*, 4th ed., Cold Spring Harbor Laboratory Press, Cold Spring Harbor, N.Y.
Greenfield, E. A. (2013) *Antibodies: A Laboratory Manual, Second edition*, Cold Spring Harbor Press, Cold Spring Harbor, NY.
Grossner, T. et al. (2016) "Pantoprazol inhibits the stimulating effect for bone formation of diclofenac in vitro evaluated by the novel method of 99m-Tc-HDP-Labeling in vitro," *Journal of Nuclear Medicine* 57(supplement 2), 1239.
Hasharoni, A. et al. (2005) "Murine spinal fusion induced by engineered mesenchymal stem cells that conditionally express bone morphogenetic protein-2," *Journal of Neurosurgery: Spine* 3(1), 47-52.
Hoemann, C. D. et al. (2009) "In vitro osteogenesis assays: Influence of the primary cell source on alkaline phosphatase activity and mineralization," *Pathologie Biologie* 57(4), 318-323.
Homan, K. A. et al. (2016) "Bioprinting of 3D Convoluted Renal Proximal Tubules on Perfusable Chips," *Scientific Reports* 6, 34845.
Hornyak, G. L. et al. (2008) *Introduction to Nanoscience and Nanotechnology*, CRC Press.
Huh, D. et al. (2011) "From Three-Dimensional Cell Culture to Organs-on-Chips," *Trends in Cell Biology* 21(12), 745-754.
Huh, D. et al. (2010) "Reconstituting Organ-Level Lung Functions on a Chip," *Science* 328(5986), 1662.
Jain, A. et al. (2016) "Assessment of whole blood thrombosis in a microfluidic device lined by fixed human endothelium," *Biomedical Microdevices* 18(4), 73.
Kim, H. J. et al. (2012) "Human gut-on-a-chip inhabited by microbial flora that experiences intestinal peristalsis-like motions and flow," *Lab on a Chip* 12(12), 2165-2174.
Kim, S. et al. (2013) "Engineering of functional, perfusable 3D microvascular networks on a chip," *Lab on a Chip* 13(8), 1489-1500.
Kimelman-Bleich, N. et al. (2009) "The use of a synthetic oxygen carrier-enriched hydrogel to enhance mesenchymal stem cell-based bone formation in vivo," *Biomaterials* 30(27), 4639-4648.
Köhler, G. et al. (1976) "Derivation of specific antibody-producing tissue culture and tumor lines by cell fusion," *European Journal of Immunology* 6(7), 511-519.
Kolesky, D. B. et al. (2016) "Three-dimensional bioprinting of thick vascularized tissues," *Proceedings of the National Academy of Sciences* 113(12), 3179.
Korin, N. et al. (2012) "Shear-Activated Nanotherapeutics for Drug Targeting to Obstructed Blood Vessels," *Science* 337(6095), 738.
Maschmeyer, I. et al. (2015) "A four-organ-chip for interconnected long-term co-culture of human intestine, liver, skin and kidney equivalents," *Lab on a Chip* 15(12), 2688-2699.
Moutsatsos, I. K. et al. (2001) "Exogenously Regulated Stem Cell-Mediated Gene Therapy for Bone Regeneration," *Molecular Therapy* 3(4), 449-461.
Nupura, S. B. et al. (2016) "A liver-on-a-chip platform with bioprinted hepatic spheroids," *Biofabrication* 8(1), 014101.
Ocak, M. et al. (2015) "Folate Receptor-Targeted Multimodality Imaging of Ovarian Cancer in a Novel Syngeneic Mouse Model," *Molecular Pharmaceutics* 12(2), 542-553.
Pelled, G. et al. (2007) "Structural and nanoindentation studies of stem cell-based tissue-engineered bone," *Journal of Biomechanics* 40(2), 399-411.
Polacheck, W. J. et al. (2014) "Mechanotransduction of fluid stresses governs 3D cell migration," *Proceedings of the National Academy of Sciences* 111(7), 2447.
Riechmann, L. et al. (1988) "Reshaping human antibodies for therapy," *Nature* 332(6162), 323-327.
Ryoo, H.-M. et al. (2006) "Critical molecular switches involved in BMP-2-induced osteogenic differentiation of mesenchymal cells," *Gene* 366(1), 51-57.
Shanmugam, V. K. et al. (2015) "Utility of a human-mouse xenograft model and in vivo near-infrared fluorescent imaging for studying wound healing," *International Wound Journal* 12(6), 699-705.
Sheyn, D. et al. (2011) "Gene-Modified Adult Stem Cells Regenerate Vertebral Bone Defect in a Rat Model," *Molecular Pharmaceutics* 8(5), 1592-1601.
Sheyn, D. et al. (2013) "PTH promotes allograft integration in a calvarial bone defect," *Molecular Pharmaceutics* 10(12), 4462-4471.
Shuler, M. L. (2017) "Organ-, body- and disease-on-a-chip systems," *Lab on a Chip* 17(14), 2345-2346.
Singleton, P. (2012) *Dictionary of DNA and Genome Technology, 3rd Edition*, Wiley-Blackwell.

(56) References Cited

OTHER PUBLICATIONS

Singleton, P. et al. (2006) *Dictionary of Microbiology and Molecular Biology Third Edition*, J. Wiley & Sons, New York, NY.
Smith, M. B. (2013) *March's Advanced Organic Chemistry: Reactions, Mechanisms, and Structure 7th Edition*, J. Wiley & Sons, New York, NY.
Sung, J. H. et al. (2013) "Microfabricated Mammalian Organ Systems and Their Integration into Models of Whole Animals and Humans," *Lab on a Chip* 13(7), 1201-1212.
Syftestad, G. T. et al. (1985) "Isolation and characterization of osteogenic cells derived from first bone of the embryonic tibia," *Developmental Biology* 110(2), 275-283.
Tai, K. et al. (2008) "Nanobiomechanics of Repair Bone Regenerated by Genetically Modified Mesenchymal Stem Cells," *Tissue Engineering Part A* 14(10), 1709-1720.
Takebe, T. et al. (2017) "Synergistic Engineering: Organoids Meet Organs-on-a-Chip," *Cell Stem Cell* 21(3), 297-300.
Trussel, A. et al. (2012) "Toward mechanical systems biology in bone," *Annals of Biomedical Engineering* 40(11), 2475-2487.
Wang, B. et al. (2016) "Secretome of Human Fetal Mesenchymal Stem Cell Ameliorates Replicative Senescen," *Stem Cells and Development* 25(22), 1755-1766.
Wobma, H. et al. (2016) "Tissue Engineering and Regenerative Medicine 2015: A Year in Review," *Tissue Engineering. Part B, Reviews* 22(2), 101-113.
Woolf, E. C. et al. (2015) "The Ketogenic Diet Alters the Hypoxic Response and Affects Expression of Proteins Associated with Angiogenesis, Invasive Potential and Vascular Permeability in a Mouse Glioma Model," *PLoS One* 10(6), e0130357.
Xie, C. et al. (2007) "Structural Bone Allograft Combined with Genetically Engineered Mesenchymal Stem Cells as a Novel Platform for Bone Tissue Engineering," *Tissue Engineering* 13(3), 435-445.
Xu, H. et al. (2006) "Magnetic resonance microscopy for monitoring osteogenesis in tissue-engineered construct in vitro," *Physics in Medicine and Biology* 51(3), 719-732.
Yakubovich, D. C. et al. (2017) "Teriparatide attenuates scarring around murine cranial bone allograft via modulation of angiogenesis," *Bone* 97, 192-200.
Yakubovich, D. C. et al. (2017) "Systemic administration of mesenchymal stem cells combined with parathyroid hormone therapy synergistically regenerates multiple rib fractures," *Stem Cell Research & Therapy* 8, 51.
Yakubovich, D. C. et al. (2015) "Computed Tomography and Optical Imaging of Osteogenesis-angiogenesis Coupling to Assess Integration of Cranial Bone Autografts and Allografts," *Journal of visualized experiments : JoVE*(106), e53459-e53459.
Zhang, X. et al. (2002) "Cyclooxygenase-2 regulates mesenchymal cell differentiation into the osteoblast lineage and is critically involved in bone repair," *Journal of Clinical Investigation* 109(11), 1405-1415.
Zhang, Y. et al. (2011) "Patterning osteogenesis by inducible gene expression in microfluidic culture systems," *Integrative biology : quantitative biosciences from nano to macro* 3(1), 39-47.
Zhang, Y. S. et al. (2016) "Bioprinting 3D microfibrous scaffolds for engineering endothelialized myocardium and heart-on-a-chip," *Biomaterials* 110, 45-59.
Zhang, Y. S. et al. (2017) "Cancer-on-a-chip systems at the frontier of nanomedicine," *Drug Discovery Today* 22(9), 1392-1399.
PCT International Search Report of International Application No. PCT/US2017/013250 dated Mar. 31, 2017.

\* cited by examiner

Figure 2
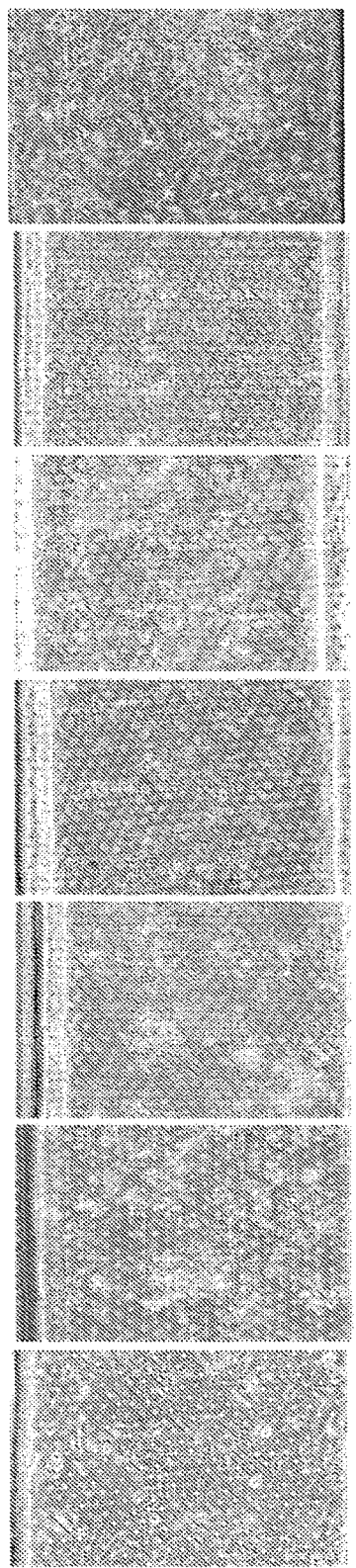
Fig. 2A
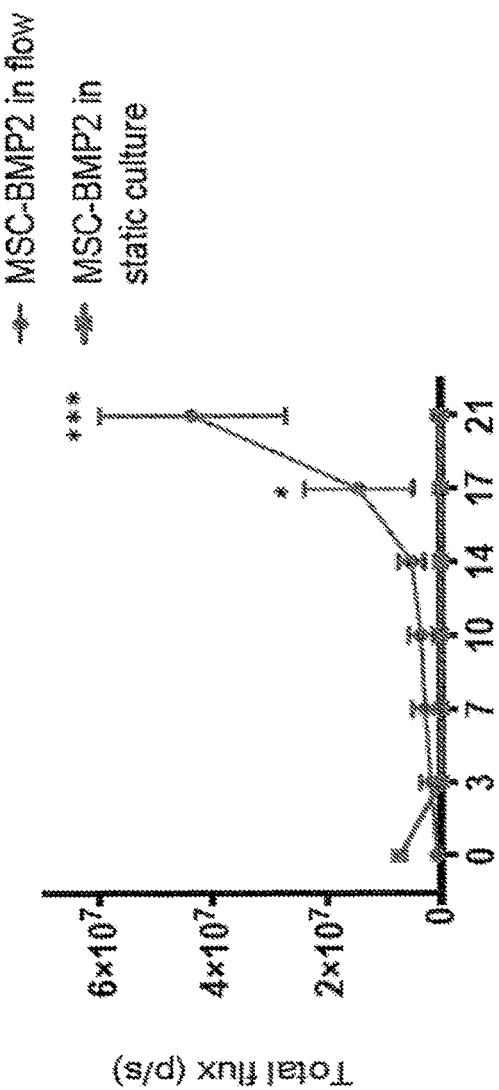
Fig. 2C Cell Survival Monitoring using BLI
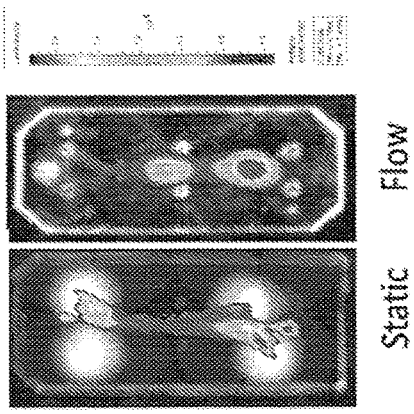
Fig. 2B

Figure 3
Fig. 3A
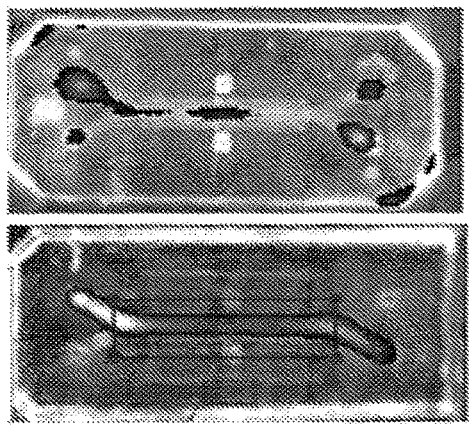
Fig. 3B
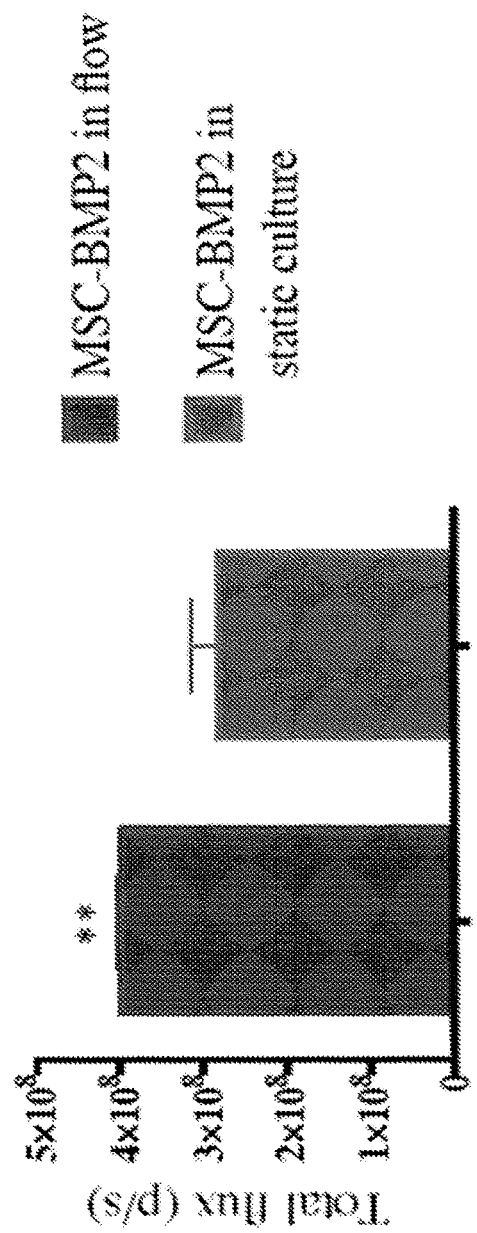

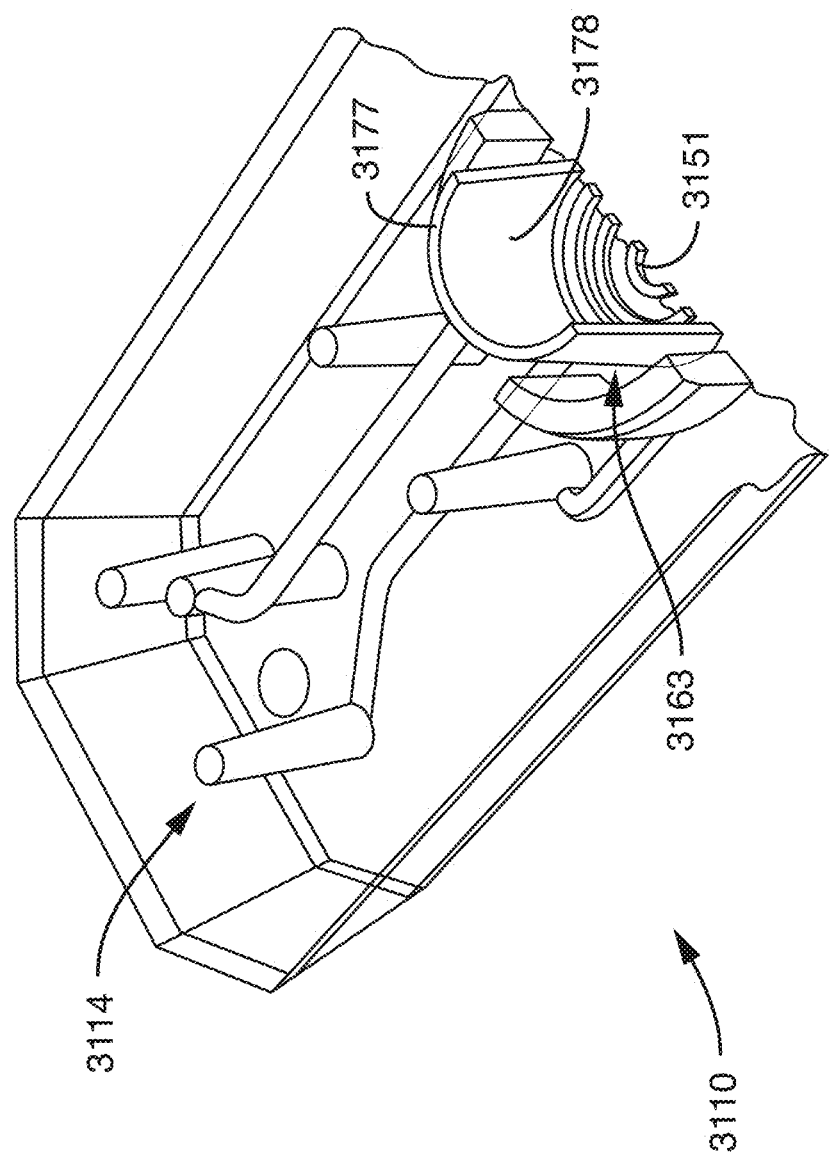

METHOD OF OSTEOGENIC DIFFERENTIATION IN MICROFLUIDIC TISSUE CULTURE SYSTEMS

PRIORITY CLAIM

This application is a continuation-in-part of, and claims priority under 35 USC 111(a) to, co-pending International Patent Application No. PCT/US17/13250, filed on Jan. 12, 2017, which claims priority to U.S. Provisional Application Ser. No. 62/277,857, filed on Jan. 12, 2016.

FIELD OF THE INVENTION

Described herein are methods and compositions related to imaging of stem cells and cells undergoing differentiation without sample manipulation.

BACKGROUND

Bones consisting of mineralized bone tissue also consists of bone marrow, nerves and blood vessels. Development and homeostasis of bone relies heavily on communication between cells in the tissues as regulated by the bone environment. Bone is an active tissue maintained by bone cells such as osteoblasts that form bone and osteoclasts that resorb bone, and it is now understood that mesenchymal stem cells (MSCs) can differentiate to various skeletal cells including osteoblasts, chondrocytes, fibroblasts, adipocytes, tenocytes, nucleus pulposus cells and more. Additionally, within the collagen and mineral matrix osteocytes are also embedded and respond to the bone environment. The balance between these cells is necessary to maintain bone function. Studying bone is a challenging field due to microarchitecture defining the bone environment, which involve the intricately dense structural composition of the bone morphology. Unlike other tissues that can be processed and prepared for experiments, including cultured cell lines, working with bone is difficult. Studying intracellular dynamics of the bone cells embedded within the mineralized tissue has proven to be a challenging task.

Compounding these challenges related to underlying properties of the cellular material, imaging cells at subcellular level within the bone environment is very difficult. Paraffin tissue slices are a long standing conventional approach to evaluate microarchitecture and bone morphology. However, sample manipulation leads to changes in biochemical properties of antigenicity and mineral structure. Newer strategies to image cells within the bone such as MPJ, Micro-CT or Ultrasound can image bone structure and recently cells, however these techniques are limited by their low resolution at the cellular level given the surrounding physiological environment.

Recent "organ-on-a-chip" technologies represent new and exciting opportunities for bone research. These devices include a microfluidic cell culture apparatus that is a more physiologically relevant in vitro model than cells cultured in dishes. Importantly, providing for continuously perfused chambers inhabited by living cells arranged to simulate tissue- and organ-level physiology allow for the culturing of bone cells in a format mirroring their physiological environment. By studying bone cell function and response in this manner, a 3D environment can reveal completely different cellular dynamics compared to 2D cultures. The availability of cellular tissue material in this format further provides new avenues for apply imaging approaches of bone microarchitecture to identify features previously unavailable in tissue cultures or at insufficient resolution in vivo. Real time imaging of the bone marrow niche within bone and fluorescent imaging of cells within the bone marrow niche has reportedly been achieved. Recent advancements in imaging techniques allows for the identification of osteocytes embedded in the bone matrix. However, determining the localization of cell types and protein expression dynamics of single cells within the bone is still very difficult. And more research is needed to identify intracellular protein activities of the cell bodies embedded within mineralized matrix.

Described herein is the use of non-destructive molecular imaging methods and systems in order to quantitatively monitor specific biological processes, over time, within the chip, without the need to harvest the tissue. Such methods can provide valuable data on developing tissues and their response to pharmaceutical, chemical and environmental agents.

SUMMARY OF THE INVENTION

Described herein is a method of detecting cellular mineralization in a microfluidic device including providing a microfluidic device including mesenchymal stem cells (MSCs), osteoblasts and/or osteocytes, adding one or more labeling agents to the microfluidic device, and detecting the labeling agent, wherein the labeling agent is capable of binding to cellular mineralization. In other embodiments, the microfluidic device further includes one or more channels for loading of a control sample. In other embodiments, the one or more labeling agents comprise bisphosphonate imaging agents. In other embodiments, the bisphosphonate imaging agent includes a pamidronate backbone with a fluorescent label. In other embodiments, the one or more labeling agents comprise a radiolabel. In other embodiments, the radiolabel includes technetium-99m ([99mTc]-BPs), [18F]-Fluoride, 99mTc-Methyl diphosphonate (Tc-MDP), and/or 68Ga-Labeled (4-{[(bis(phosphonomethyl))carbamoyl]methyl}-7,1 O-bis(carboxymethyl)-I,4, 7, I 0-tetraazacyclododec-1-yl)acetic acid (BP AMD) ([68Ga]BPAMD). In other embodiments, detecting the labeling agent includes Micro CT, Micro SPECT, and/or PET imaging. In other embodiments, detecting the labeling agent further includes comparison of the quantity of detected labeling agent with one or more control samples. In other embodiments, further culturing of MSCs, osteoblasts, osteocytes, chondrocytes, tenocytes, fibroblasts, notochordal cells, and/or nucleus pulposus cells in the microfluidic device. In other embodiments, the method includes further detection of the labeling agent.

Also described herein is a method of detecting secreted extracellular macromolecules in a microfluidic device including providing a microfluidic device including stem cells, applying one or more pulse sequences to the microfluidic device; and, detecting the pulse sequence signal intensity, wherein the pulse sequence signal intensity is capable of measuring one or more macromolecules secreted by the stem cells. In other embodiments, the stem cells are mesenchymal stem cells (MSCs). In other embodiments, the stem cells are pluripotent stem cells (pSCs). In other embodiments, the stem cells are induced pluripotent stem cells (iPSCs). In other embodiments, detecting the pulse sequence signal intensity includes chemical exchange saturation transfer (CEST), pH measurement of Tl rho, magnetization transfer contrast (MTC), and/or magnetization exchange (MEX). In other embodiments, CEST detects a quantity of glycosaminoglycans (GAGs). In other embodiments, pH measurement of Tl rho detects a quantity of GAGs. In other embodiments, MTC detects a quantity of collagen. In other embodiments, MEX detects a quantity of collagen and/or osteoid. In other embodiments, the microfluidic device further includes one or more channels for loading of a control sample. In other embodiments, detecting the pulse sequence signal intensity further includes comparison of the quantity of detected pulse sequence signal intensity with one or more control samples. In other embodiments, the method includes further culturing of stem cells in the microfluidic device. In other embodiments, the method includes further detection of pulse sequence signal intensity.

In one embodiment, the present invention contemplates a method of osteogenic differentiation comprising: a) seeding mesenchymal stem cells (MSCs) on a surface of a microfluidic device in culture medium in the absence of Bone Morphogenetic Protein-2 (BMP2) and the absence of flow until the MSCs attach to said surface; b) flowing the culture medium in the absence of BMP2 such that the MSCs proliferate so as to create an expanded culture of cells; and c) contacting the expanded culture of MSCs with osteogenic medium containing BMP2 at a flow rate such that at least a portion of said expanded culture of cells differentiate into cells of the osteoblast lineage. In one embodiment, said differentiated cells of the osteoblast lineage express one or more of osteocalcin, bone sialoprotein (bsp), osteopontin (opn), and collagen type 1. In one embodiment, said differentiated cells exhibit osteogenic ECM secretion (e.g. as shown in FIG. 7A-F). In one embodiment, said flow rate causes the differentiated cells to express a higher level of at least one of osteocalcin, bone sialoprotein (bsp), osteopontin (opn), and collagen type I as compared to cells exposed to said osteogenic medium in the absence of flow.

In a further embodiment, the invention provides a method of osteogenic differentiation comprising: a) seeding mesenchymal stem cells (MSCs) on a surface of a microfluidic device in culture medium in the absence of Bone Morphogenetic Protein-2 (BMP2) and the absence of flow until the MSCs attach to the surface to produce attached MSCs; b) flowing the culture medium in the absence of BMP2 such that the attached MSCs proliferate so as to create proliferated attached MSCs; and c) contacting the proliferated attached MSCs with osteogenic medium containing BMP2 at a flow rate such that at least a portion of the proliferated attached MSCs differentiate into differentiated cells comprising one or more cell types of osteoblast lineage. In one embodiment, the differentiated cells express one or more of osteocalcin, bone sialoprotein (bsp), osteopontin (opn), and collagen type 1. In one embodiment, the differentiated cells exhibit osteogenic ECM secretion. In one embodiment, the flow rate in step c) causes the differentiated cells to express a higher level of at least one of osteocalcin, bone sialoprotein (bsp), osteopontin (opn), and collagen type I as compared to proliferated attached MSCs that are contacted with the osteogenic medium containing BMP2 in the absence of flow.

In a further embodiment, the invention provides a method of osteogenic differentiation comprising a) Seeding mesenchymal stem cells (MSCs) on a laminin-coated porous flexible membrane in an microfluidic device in culture medium in the absence of Bone Morphogenetic Protein-2 (BMP2) and the absence of flow until the MSCs attach to the membrane, b) Flowing the culture medium in the absence of BMP2 such that the MSCs proliferate to produce confluent MSCs, and c) Contacting the confluent MSCs with osteogenic medium containing BMP2 to produce differentiated cells that express one or more of osteocalcin, bone sialoprotein (bsp), osteopontin (opn), and collagen type 1. In one embodiment, the differentiated cells express a higher level of at least one of osteocalcin, bone sialoprotein (bsp), osteopontin (opn), and collagen type 1 compared to the MSCs. In one embodiment, the contacting step is in the presence of flow of the osteogenic medium. In one embodiment, the contacting step is in the absence of flow of the osteogenic medium. In one embodiment, the differentiated cells express a higher level of at least one of osteocalcin, bone sialoprotein (bsp), osteopontin (opn), and collagen type 1 in the presence of flow of the osteogenic medium compared to in the absence of flow of the osteogenic medium. In one embodiment, the osteogenic medium contains β-glycerophosphate and L-Ascorbic acid. In one embodiment, the method further comprises non-invasive determination of one or more of the survival status, proliferation status, and differentiation status of the differentiated cells in the microfluidic device.

The invention also provides, in one embodiment, a method of osteogenic differentiation comprising a) seeding mesenchymal stem cells (MSCs) on a surface of a microfluidic device in culture medium in the absence of Bone Morphogenetic Protein-2 (BMP2) and the absence of flow until the MSCs attach to the surface to produce attached MSCs; b) flowing the culture medium in the absence of BMP2 such that the attached MSCs proliferate so as to create proliferated attached MSCs; and c) contacting the proliferated attached MSCs with osteogenic medium containing BMP2 at a flow rate such that at least a portion of the proliferated attached MSCs differentiate into differentiated cells comprising one or more cell types of osteoblast lineage. In one embodiment, the differentiated cells express one or more of osteocalcin, bone sialoprotein (bsp), osteopontin (opn), and collagen type 1. In one embodiment, the differentiated cells exhibit osteogenic ECM secretion. In one embodiment, the flow rate in step c) causes the differentiated cells to express a higher level of at least one of osteocalcin, bone sialoprotein (bsp), osteopontin (opn), and collagen type I as compared to proliferated attached MSCs that are contacted with the osteogenic medium containing BMP2 in the absence of flow.

The invention also provides method of osteogenic differentiation comprising a) seeding mesenchymal stem cells (MSCs) in an microfluidic device in culture medium in the absence of Bone Morphogenetic Protein-2 (BMP2) and the absence of flow, b) flowing the culture medium in the absence of BMP2 such that the MSCs proliferate to produce proliferated MSCs, and c) contacting the proliferated MSCs with osteogenic medium containing BMP2 to produce differentiated cells that express one or more of osteocalcin, bone sialoprotein (bsp), osteopontin (opn), and collagen type 1. In one embodiment, said seeding comprises seeding said MSCs on a first surface of said microfluidic device. In one embodiment, said first surface comprises a porous flexible membrane. In one embodiment, said membrane is coated with extracellular matrix. In one embodiment, said extracellular matrix comprises one or more of laminin, collagen, fibronectin, fibrin, vitronectin, hyaluronic acid, peptides, gelatin, Matrigel®, decellularized bone marrow, and demineralized bone powder. In one embodiment, said extracellular matrix comprises laminin. In one embodiment, said flowing comprises flowing until said proliferated MSC produce confluent MSCs. In one embodiment, said first surface is coated with at least one extracellular matrix (ECM). In one embodiment, said extracellular matrix comprises one or more of laminin, collagen, fibronectin, vitronectin, hyaluronic acid, peptides, gelatin, Matrigel®, and decellularized bone marrow. In one embodiment, said seeding comprises seeding said MSCs in a three-dimensional (3D)

matrix. In one embodiment, said 3D matrix comprises 3D gel. In one embodiment, said 3D matrix comprises decellularized matrix. In one embodiment, said 3D matrix comprises 3D extracellular matrix (ECM). In one embodiment, said microfluidic device comprises a culture compartment, and said MSCs are comprised in said culture compartment. In one embodiment, said culture compartment comprises an opening configured to provide direct access to one or more of said culture compartment and said MSCs.

In one embodiment, the method further comprises applying mechanical stimulation to one or more of said MSCs, attached MSCs, proliferated attached MSCs, and differentiated cells. In one embodiment, said first surface is a surface of a first channel. In one embodiment, said microfluidic device comprises endothelial cells attached to a second channel that is in fluidic communication with said first channel. In one embodiment, said membrane comprises endothelial cells attached to a second surface of said membrane.

BRIEF DESCRIPTION OF FIGURES

FIG. 2A-C. Cell survival and proliferation on the organ-on-chip. FIG. 2A. Micrographs of the cells on the chip grown for 3 weeks in osteogenic conditions. FIG. 2B. bioluminescent imaging (BLI) images taken on Day 0. FIG. 2C. Quantitative analysis BLI that was done twice a week for 3 weeks. Bars indicate standard deviation, n=5, $*p<0.05$; $***P<0.001$.

FIG. 3A-D. Osteogenic differentiation at Week 3 measured with two probes (OsteoSense and BoneTag) using two different imaging systems: fluorescent imaging system (IVIS, Perkin Elmer) and Near Infrared imaging system (Odyssey® CLx, Li-Cor). FIG. 3A. FLI images of chips incubated with BoneTag and in FIG. 3B the labeling was quantified FIG. 3C. using fluorescent imaging IVIS Live staining where live cells are stained with FITC (green) dye and OsteoSense is depicted in red and imaged using confocal microscopy, 10× magnification. In FIG. 3D, labeling was quantified, bars indicate standard deviation, n=5, $*p<0.05$; $***P<0.001$.

(FIG. 6A). Bioluminescent images taken on the same time points using IVIS imager. The images are relative and the scale of the color code is depicted on the right side of each group (FIG. 6B). Quantitative analysis of total BLI imaging that was done for two weeks (FIG. 6C, bars indicate SD, n=5, $*p<0.01$; $**P<0.001$).

FIG. 12A-B illustrates a cut-away view of one embodiment of a stretchable open-top microfluidic device showing the regional placement of assay cells (e.g., MSCs, osteoblast lineage cell types, epithelial cells, dermal cells and/or endothelial cells).

DEFINITIONS

Figure 1:
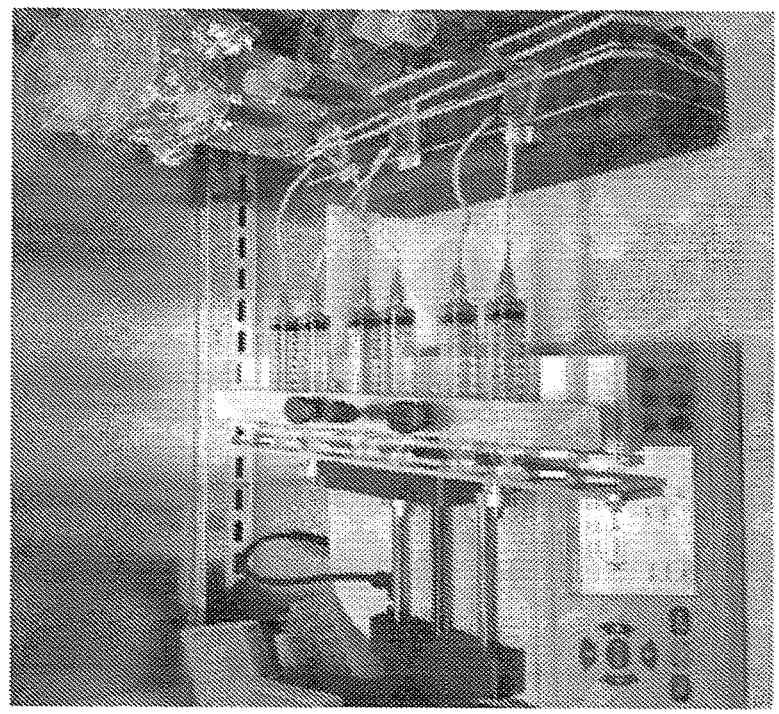
FIG. 1. Organ-on-chip dimensions and setting of the flow system. The flow was set to 30 µl/h and the media in the reservoirs was replaced or refilled twice a week.
Figure 1:
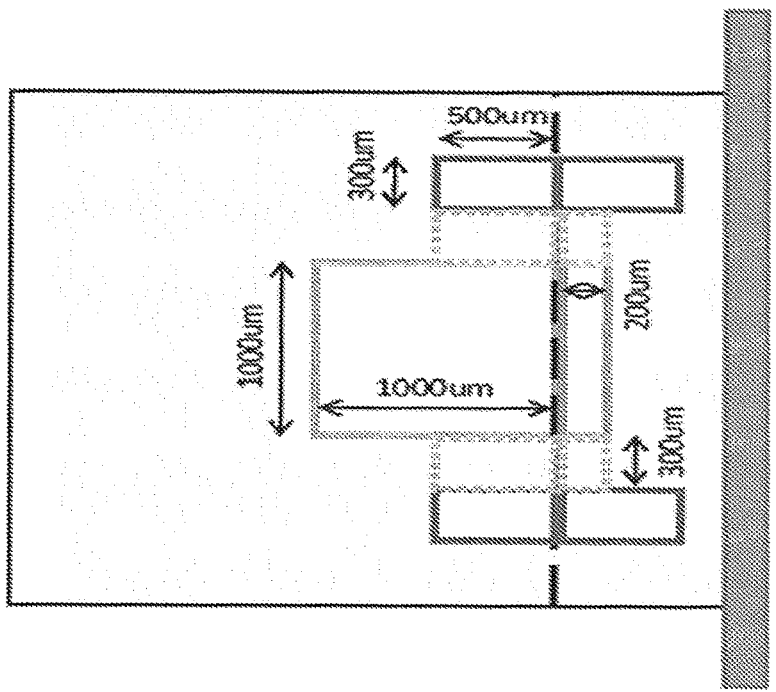
Figure 1:
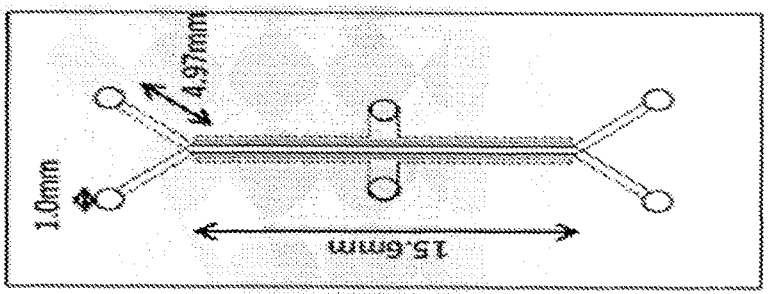

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

"Mesenchymal stem cells" ("MSCs") are an example of tissue or adult stem cells. They are "multipotent," meaning they can produce more than one type of specialized cell of the body, but not all types. MSCs make the different specialized cells found in the skeletal tissues.

The term "proliferation" refers to an increase in cell number.

The term "differentiation" refers to the maturation process cells undergo whereby they become specialized to develop distinctive characteristics and/or perform specific functions. In some embodiment, differentiated cells are less likely to divide that undifferentiated cells. Differentiation involves the production of cell-specific and/or tissue-specific proteins.

"Microfluidic" device refers to a device for manipulating fluids having a volume in the range of microliters ($10^{-6}$) to picoliters ($10^{-12}$), and that contains at least one channel having at least one dimension of 10 μm or more.

"Confluence" and "confluent" as used herein in reference to adherent cells refers to a condition wherein cells throughout a culture are substantially in contact with each other creating what appears to be a continuous sheet, such as a "monolayer" of cells.

"Expression" refers to the process by which DNA is made into a functional gene product, such as protein or RNA. Expression may be detected by detecting the level of the transcribed RNA and/or the level of the translated protein.

"Laminin" refers to high-molecular weight (~400 to ~900 kDa) proteins of the extracellular matrix (ECM). Laminin is a major component of the basal lamina (one of the layers of the basement membrane), and is a protein network foundation for most cells and organs.

"Non-invasive" determination of the status of cells refers to the process of determining the condition (e.g., viability, protein expression, morphology, etc.) of the cells without harvesting the cells and/or without reducing cell viability and/or without structural and/or functional damage to the system in which the cells are contained.

The term "control" in reference to a sample (e.g., mixture of components, cell, etc.) refers to any type of sample that one of ordinary skill in the art may use for comparing to a test sample (e.g., cell, tissue, animal, virus, etc.) by maintaining the same conditions in the control and test samples, except in one or more particular variable factor or component. In one embodiment, the comparison of the control and test samples is used to infer a causal significance of this variable.

Figure 9:
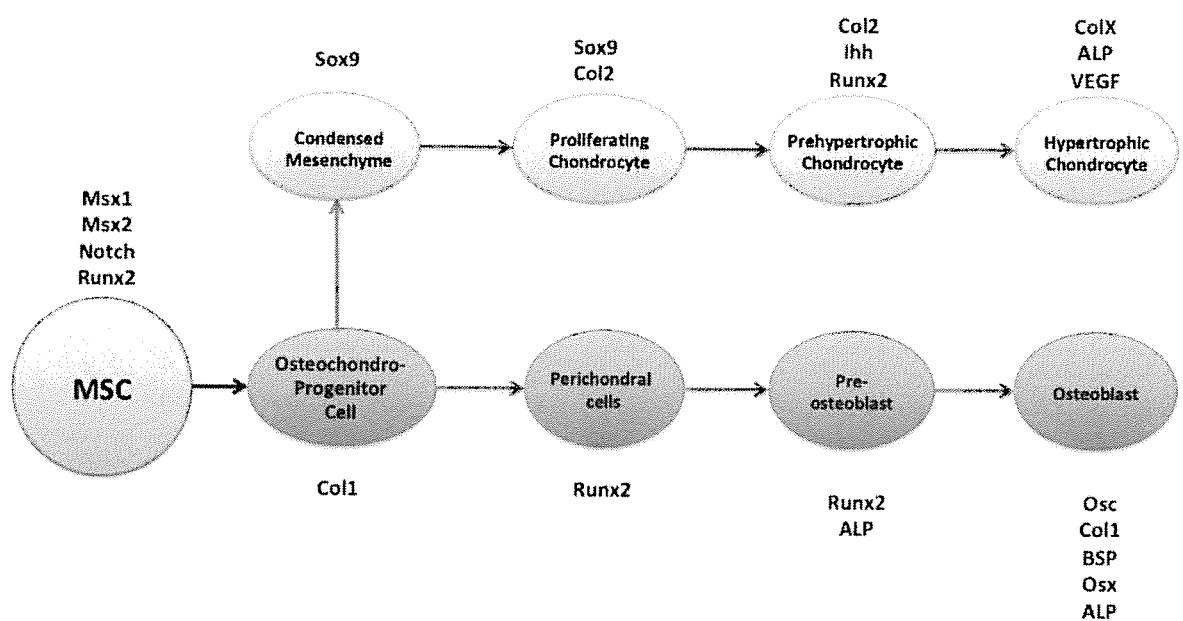
FIG. 9. Differentiation of MSCs into cells of the osteoblast lineage and chondrocyte lineage, including exemplary factors whose expression is elevated relative to one or more of the preceding cell types in the differentiation lineage.

"Osteoblast lineage" cell type refers to a cell that is produced during differentiation of mesenchymal stem cells (MSCs) into osteoblasts, and is exemplified by an osteochondro-progenitor cell expressing an increased level of Col1 compared to MSCs, perichondral cell expressing an increased level of Runx2 compared to an osteochondro-progenitor cell and/or MSC, pre-osteoblast expressing an increased level of Runx2 and/or ALP compared to perichondral cell and/or osteochondro-progenitor cell and/or MSC, and osteoblast expressing an increased level of Osc and/or Col1 and/or BSP and/or Osx and/or ALP compared to a pre-osteoblast and/or perichondral cell and/or osteochondro-progenitor cell and/or MSC (Exemplified in FIG. 9).

"Bone morphogenetic protein" and "BMP" refer to a BMP polypeptide or a fragment thereof that is similar or identical to the sequence of a wild-type BMP or fragment thereof. For example, a BMP polypeptide or fragment thereof has an amino acid sequence that is at least 70% or more (including at least 75%, at least 80%, at least 85%, at least 90%, at least 95%, at least 97%, at least 99%, or 100%) identical to that of a wild-type BMP, and is capable of having the normal functioning of BMP. The BMP used in the methods of various aspects described herein can be naturally occurring or recombinant protein or peptide.

"Matrix" refers to a collection of molecules (including polymers) that provide structural and/or biochemical support to the surrounding cells.

"Extracellular matrix" and "ECM" interchangeably refer to a matrix secreted by cells. In some embodiments, the ECM functions in enhancing cell adhesion and/or cell-to-cell communication and/or cell differentiation. ECM can be applied in two-dimensional (2D) cell culture to cover cell culture surfaces (e.g., membranes, solid supports, etc.) and/or in three-dimensional (3D) cell culture to encapsulate cells and/or tissue and/or organoids. ECM includes "natural ECM" and "synthetic ECM." "Natural ECM" and "native ECM" interchangeably refer to ECM in which the molecular components are derived from natural sources, and is exemplified by laminin, collagen, fibronectin, fibrin, vitronectin, hyaluronic acid, peptides, gelatin, and Matrigel®, decellularized matrix (e.g., decellularized bone marrow), and demineralized bone powder. Natural ECM is commercially available (East River Biosciences, MA, USA). "Synthetic ECM" refers to ECM containing man-made polymers, such as poly(ethylene glycol) (PEG), poly(vinyl alcohol), and poly(2-hydroxy ethyl methacrylate).

"Decellularized matrix" refers to a composition containing a molecules (including polymers) that are derived from or generated by removing the cellular components of an isolated population of cells and/or organs and/or tissues (e.g., bone marrow tissue) without significant damage to the extracellular matrix that is produced by the cells and/or organs and/or tissues. By way of non-limiting example, bone marrow cells can be removed from bone marrow tissue by chemical and/or physical means using methods known in the art for partially or completely decellularizing a tissue such as those described in Ingber et al. U.S. Pat. Appl. No. 20140186414, published Jul. 3, 2014, incorporated by reference. Briefly, cells can be removed and/or made nonviable by, for example, 1) washing the tissue with detergents or 2) washing the tissue with a buffer, then fixing the tissue with paraformaldehyde. In some embodiments, the tissue can be decellularized by fixing with 4% paraformaldehyde (PFA) for 48 hours at 4° C. and then immersing the microfluidic device and/or tissue in 70% ethanol for 24 hours at 4° C. and three times in PBS at 4° C. for 2 hours each time to wash out the PFA. The remaining decellularized bone marrow scaffold can be used ex vivo and/or in vitro and be repopulated by cells (such as bone marrow cells and/or blood cells) provided from another source.

"Demineralized bone powder," "demineralized bone matrix powder" and "DMB powder" can be obtained commercially (RTI Surgical). DMB powder can also be prepared using methods known in the art by excising, fragmenting, and sieving mammalian femurs (e.g., from mouse) to obtain particles less than 250 μm in diameter. The powder can then be demineralized using 0.5 N HCl (Eagle et al. "Production of an osteoinductive demineralised bone matrix powder without the use of organic solvents," Cell Tissue Bank. 2015 September; 16(3):433-41).

"Gel" refers to a coherent mass containing a liquid in which particles too small to be seen in an ordinary optical microscope are dispersed and/or arranged in a fine network throughout the mass. A gel may be notably elastic and jellylike (as gelatin or fruit jelly), or quite solid and rigid (as silica gel, a material that looks like coarse white sand). In one embodiment, gels are colloids (aggregates of fine particles, as described above, dispersed in a continuous medium) in which the liquid medium has become viscous enough to behave substantially as a solid.

"Mechanical stimulation" refers to one or more of compression, tension, shear, and hydrostatic loading that may be applied in constant and/or changing rates and/or magnitudes and/or amplitudes, and/or frequency, and/or loading duration and/or total duration to cells in a device, to alter cell proliferation, differentiation, gene expression, biochemistry, and/or biomechanics as shown in FIGS. 13-18, and previously described (Anderson & Johnstone, Bioeng. Biotechnol., 11 Dec. 2017, "Dynamic Mechanical Compression of Chondrocytes for Tissue Engineering: A Critical Review;" Tuan et al. U.S. Pat. Application No. 20160201037, incorporated by reference).

The terms "higher," "greater," "increase," "elevate," "raise," and grammatical equivalents when in reference to the level of any molecule (e.g., amino acid sequence such as osteocalcin, bone sialoprotein (bsp), osteopontin (opn), collagen type 1, runt-related transcription factor 2 (Runx2), alkaline phosphatase (ALP), Osc, and osterix (Osx), nucleic acid sequence such as a that encoding such as osteocalcin, bone sialoprotein (bsp), osteopontin (opn), collagen type 1, runt-related transcription factor 2 (Runx2), alkaline phosphatase (ALP), Osc, and osterix (Osx), etc.), cell, and/or phenomenon (e.g., level of gene transcription, level of RNA translation, level of protein expression, etc.), in a first sample relative to a second sample, mean that the quantity of the molecule, cell and/or phenomenon in the first sample is higher than in the second sample by any amount that is statistically significant using any art-accepted statistical method of analysis. In one embodiment, the first sample is exemplified by, but not limited to, a sample that has been manipulated using the invention's systems and/or compositions and/or methods. In a further embodiment, the second sample is exemplified by, but not limited to, a sample that has not been manipulated using the invention's compositions and/or methods, such as a control sample. In one embodiment, the quantity of the molecule, cell and/or phenomenon in the first sample is at least 10% greater than in the second sample, including from at least 10% greater to 1,000-fold greater than in the second sample. In one embodiment, the quantity of the molecule, cell and/or phenomenon in the first sample is at least 10% greater, at least 20% greater, at least 30% greater, at least 40% greater, at least 50% greater, at least 60% greater, at least 70% greater, at least 80% greater, at least 90% greater, at least 1-fold greater, at least 2-fold greater, at least 3-fold greater, at least 4-fold greater, at least 5-fold greater, at least 6-fold greater, at least 6-fold greater, at least 8-fold greater, at least 9-fold greater, at least 10-fold greater, at least 11-fold greater, at least 12-fold greater, at least 13-fold greater, at least 14-fold greater, at least 15-fold greater, at least 16-fold greater, at least 17-fold greater, at least 18-fold greater, at least 19-fold greater, and at least 20-fold greater than in the second sample.

DETAILED DESCRIPTION

All references cited herein are incorporated by reference in their entirety as though fully set forth. Unless defined otherwise, technical and scientific terms used herein have the same meaning as commonly understood by one of ordinary skill in the art to which this invention belongs. Allen et al, Remington: The Science and Practice of Pharmacy $22^{nd}$ ed., Pharmaceutical Press (Sep. 15, 2012); Hornyak et al, Introduction to Nanoscience and Nanotechnology, CRC Press (2008); Singleton and Sainsbury, Dictionary of Microbiology and Molecular Biology $3^{rd}$ ed., revised ed., J. Wiley & Sons (New York, NY 2006); Smith, March's Advanced Organic Chemistry Reactions, Mechanisms and Structure $7^{th}$ ed., J. Wiley & Sons (New York, NY 2013); Singleton, Dictionary of DNA and Genome Technology $3^{rd}$ ed., Wiley-Blackwell (Nov. 28, 2012); and Green and Sambrook, Molecular Cloning: A Laboratory Manual 4th ed., Cold Spring Harbor Laboratory Press (Cold Spring Harbor, NY 2012), provide one skilled in the art with a general guide to many of the terms used in the present application. For references on how to prepare antibodies, see Greenfield, Antibodies A Laboratory Manual $2^{nd}$ ed., Cold Spring Harbor Press (Cold Spring Harbor NY, 2013); Kohler and Milstein, Derivation of specific antibody-producing tissue culture and tumor lines by cell fusion, Eur. J. Immunol. 1976 Jul., 6(7):511-9; Queen and Selick, Humanized immunoglobulins, U.S. Pat. No. 5,585,089 (1996 December); and Riechmann et al, Reshaping human antibodies for therapy, Nature 1988 Mar. 24, 332(6162):323-7.

One skilled in the art will recognize many methods and materials similar or equivalent to those described herein, which could be used in the practice of the present invention. Indeed, the present invention is in no way limited to the methods and materials described.

In recent years, microfluidic devices have been developed with the aim to replicate human tissues in vitro. These systems, also called microfluidic chips or "organ-on-a-chip", have the potential to serve as an alternative for animal models that are used to test pharmaceutical, chemical and environmental agents. The microfluidic chips are attractive for biomedical research and drug discovery due to low cost and ethical considerations compared to animal models. A variety of examples are described in Bhatia and Ingber, "Microfluidic organs-on-chips." Nat Biotechnol. 2014 August; 32(8):760-72, which is fully incorporated by reference herein.

An important caveat of the "chips" is that currently there is no option to quantitatively monitor biological processes that take place within the chip, over time. To date, researchers are using destructive methods in order to analyze tissue formation, gene expression, protein secretion etc. These methods include histology, immunofluorescence or PCR and require the harvest of the "tissue" at a certain time point. The use of non-destructive molecular imaging methods and systems in order to quantitatively monitor specific biological processes, over time, within the chip, without the need to harvest the tissue would be a significant improvement in the field. Such methods can provide valuable data on developing tissues and their response to pharmaceutical, chemical and environmental agents.

Mesenchymal stem cells (MSCs) can differentiate to various skeletal cells including osteoblasts, chondrocytes, fibroblasts, adipocytes, tenocytes, nucleus pulposus cells and more. In situ imaging, both in non-living and living specimens, have provided new insights, but for the above described reasons, quantitative experimental data requires destructive processing that may introduce bias, and lack temporal and spatial resolution. In this regard, microfluidic organ-on-a-chip coupled with non-destructive labeling and imaging techniques may allow precise capture of MSC, osteoblast and osteocyte cell populations in micro and ultrastructure in 2D and 3D. Live cell imaging techniques which are able to track structural morphology and cellular differentiation in both space and time combined with the latest biochemical assays and microfluidic imaging techniques can provide further insight on the biological function of MSC, MSCs, osteoblasts, osteocytes, chondrocytes, tenocytes, fibroblasts, notochordal cells, and/or nucleus pulposus cells.

Existing techniques for imaging of cells in skeletal and other tissues has proved challenging due to the need to develop methodologies for sectioning specimens, labeling or imaging of specimens or to develop protocols for decalcifying specimens to enable conventional sectioning and imaging techniques to be used. Current imaging approaches rely mainly on histological stains combined with conventional light microscopy. Confocal imaging approaches allows for three-dimensional (3D) imaging in situ within the bone environment. In contrast to inherently two-dimensional (2D) imaging techniques such as light microscopy, confocal microscopy stacks optical sections at different focal planes to generate a three-dimensional (3D) representation of the sample. Endogenous (auto)fluorescence of the bone tissue can be used to provide contrast for confocal microscopy measurements. More often, various fluorescent staining agents are used in conjunction with modem confocal laser scanning microscopy (CLSM), such as rhodamine and fluorescein, which can be incubated with undecalcified bone sections. More specific staining agents, such as fluorescein isothiocyanate (FITC)-conjugated phalloidin and DAPI, label the actin skeleton and/or DNA of cell nuclei in such a way that the components cells can be directly imaged and separately displayed in 3D However, a major drawback with CLSM is the limited maximum focal plane depth of around 100-150$\mu m$. Additionally, CLSM is tainted with image artifacts, such as signal attenuation with increasing focal plane depth or aberrations due to refractive index mismatch. Such artifacts are absent in (conventional) X-ray absorption-based computed tomography (CT). Micro-computed CT ($\mu$CT) and 3D morphometric measures to quantify trabecular microarchitecture have laid the foundations for $\mu$CT to become a standard for bone morphometry. In bone research, the standard application of desktop $\mu$CT systems with typical voxel sizes in the order of 5-100$\mu m$ is a core approach for quantitative characterization of whole bone geometry. Synchrotron radiation-based CT allows for imaging of bone microstructure, canal networks, as well as study of populations such as osteocytes within bone. Most recently, optimized imaging protocol for SR CT provides spatial resolution closer to the diffraction limit of visible light at a few hundred nanometers. The recent availability of desktop $\mu$CT scanners with voxel sizes below 1$\mu m$ allow for new opportunities for imaging.

Over the past two decades or so, technologies for imaging of living cells using light and confocal microscopy have advanced at a rapid rate. Coupled with enhanced green fluorescent proteins (GFPs) and a seemingly limitless array of fluorescent imaging probes has made it possible to image almost any intracellular or extracellular structure or protein in living cells and tissues. A large selection of fluorescent probes and reagents are commercially available to the researcher for investigating biological events in living cells, including fluorescent antibodies, kits for fluorescently labeling proteins of interest, dyes for cell and nuclear tracking, probes for labeling of membranes and organelles, fluorescence reagents for determining cell viability, probes for assessing pH and ion flux and probes for monitoring enzyme activity, etc. In addition, a variety of GFP-derived fluorescent protein vectors are available that can either be used as reporter constructs or to generate fusion constructs with a protein of interest. These enable the live monitoring of gene expression and protein localization in vivo, and in real time.

The traditional approach of collecting "static" images of fixed or post mortem cells and tissues provides a snapshot view of events at a single fixed point in time. However, this inherently overlooks the dynamic aspects of the biology being examined. In contrast, live cell imaging enables the visualization of temporal changes in living specimens and can reveal novel aspects of the biology that may not otherwise have been appreciated. Additionally, the datasets generated from time-lapse imaging are information rich and can be interrogated quantitatively to enable measurement of cellular, subcellular and tissue dynamic events as a function of time Although these approaches are leading to exciting discoveries that are advancing our understanding of biological systems, there are several limitations that need to be acknowledged. Firstly, fluorescent probes may perturb or alter the biology being examined. Validation studies are needed to make sure that the fusion protein still functions similarly to the wild type form. It is also advantageous to confirm findings with more than one type of imaging probe if possible. For example, a GFP fusion protein can be used for in vivo localization of a specific protein and key data can be confirmed using a fluorescence-conjugated antibody against the same protein. When developing live cell imaging protocols, there is always a compromise between obtaining a high enough signal-to-noise ratio to enable quantitative measurements and to obtain sufficient image resolution, while at the same time avoiding phototoxic effects to the cells. Therefore, to ensure cell viability, the researcher may have to accept a lower image quality and resolution than would be acceptable for equivalent images of fixed specimens. Nevertheless, technologies such as multiphoton fluorescence microscopy can increase the depth of tissue penetration for live cell imaging applications and reduce phototoxicity by using a longer wavelength light to excite fluorophores. These instruments are becoming more widely used for live imaging applications due to their advantages over conventional widefield and confocal microscopy systems.

Recently, live cell imaging approaches have been applied to the study of MSCs, osteoblasts and osteocytes. Organ cultures of neonatal calvaria from mice have provided a useful model for imaging the dynamic properties of osteocytes. Another way in which this model can be used for imaging osteocyte dynamics is by using long term cultures of MSCs and osteoblasts. These cells differentiate when cultured under mineralizing conditions to form mineralized nodules in which the transition to the osteocyte-like phenotype can be monitored by fluorescent labeling or radiolabeling. To gain maximum information, imaging of these can be combined with other fluorescent probes, such as alizarin red to monitor mineral deposition. Live cell imaging studies as applied to investigating osteocyte biology are still in their infancy. In addition to revealing the dynamic properties of MSCs, osteoblasts and osteocytes, identifying the underlying intracellular signaling pathways, such as calcium oscillations, monitoring the temporal integration of osteocyte differentiation and mineralization, live imaging studies have considerable potential to address many as yet unresolved questions in osteocyte biology.

Most importantly, biochemical data characterizing the precise role of MSCs, osteoblasts and osteocytes in bone remodeling remains severely limited. A number of in vivo models have been developed to study their function. Existing technologies typically harvest large osteocyte populations and employ technologies which provide a comprehensive assessment of a large number of genes which are both up-regulated and down-regulated in response mechanical stimulation. For example, to comprehensively assess osteocyte gene expression in a mouse model for load induced bone adaptation, current state-of-the-art approaches extract large populations of osteocytes from loaded bone and perform micro-array-analysis to quantify the expression levels of tens of thousands of different genes. Global gene expression assays derived from in vivo models for bone adaptation have identified a number of candidate genes and revealed potential load regulated pathways. Nevertheless, there are significant limitations when interpreting these data. The harvesting and analysis of large populations of osteocytes reports gene expression averaged over tens of thousands of cells, each of which reside in different micro-environments characterized by different levels of mechanical strain and local osteoblastic/osteoclastic activity. It is therefore possible that key genes and networks are being concealed. Emerging studies investigate local regulation of gene expression in osteocytes by comparing 2D histology sections from loaded bone stained for specific molecular targets (sclerostin) with micro finite element (µFE) models. Whilst informative, these approaches are still very much qualitative and only permit the analysis of one specific molecular target at a time.

Addressing these limitations are microfluidic imaging approaches which allow for spatial and temporal mapping in three dimensions and quantitative measurement of gene expression cells in an organized "organ-on-a-chip" niche. Examples of a "microfluidic imaging" approach can be briefly described by the following workflow: bone formation and/or resorption are spatially mapped and quantified in technologies such as in vivo µCT and 3D image registration techniques; labeling (e.g., fluorescence, radio labeling) or other techniques, (e.g., chemical exchange saturation transfer (CEST), pH measurement Tl rho, magnetization transfer contrast, magnetization exchange or other technologies. The vast amount of data generated using these approaches can be used to build, feed and validate computational models of various skeletal and other tissues, which incorporate all of the different length scales, from the organ-level to the cellular-level. Further examples include those described in Trussel et al., "Toward mechanical systems biology in bone." Ann Biomed Eng. 2012 November; 40(11):2475-87. Described herein is a method of detecting properties of one of more cells in a microfluidic device. In other embodiments, the microfluidic device includes mesenchymal stem cells (MSCs), osteoblasts and/or osteocytes. In other embodiments, the microfluidic device includes cartilage, tendon/ligament, nucleus pulposus, annulus fibrosus, chondrocytes, tenocytes, fibroblasts, and/or notochordal cells among others. It is emphasized that the described methods and techniques find wide applicability to biological tissues. In other embodiments, the microfluidic device includes stem cells. In other embodiments, the stem cells are mesenchymal stem cells (MSCs). In other embodiments, the stem cells are induced pluripotent stem cells (iPSCs). In other embodiments, the microfluidic device further includes one or more channels for loading of a control sample. In various embodiments, the properties are biochemical properties of the one or more cells in a microfluidic device.

In various embodiments, the method includes providing a microfluidic device, adding one or more labeling agents to the microfluidic device, and detecting the labeling agent, wherein the labeling agent is capable of binding to one or more biochemical properties of one or more cells in the microfluidic device. In other embodiments, one or more labeling agents comprise bisphosphonate imaging agents. In other embodiments, the bisphosphonate imaging agent includes a pamidronate backbone with a fluorescent label. In other embodiments, the one or more labeling agents comprise a radiolabel. In other embodiments, the radiolabel includes technetium-99m ([99mTc]-BPs), [18F]-Fluoride, 99mTc-Methyl diphosphonate (Tc-MDP), and/or 68Ga-Labeled (4-{[(bis(phosphonomethyl))carbamoyl]methyl}-7,1 0-bis(carboxymethyl)-I,4, 7, I 0-tetraazacyclododec-1-yl) acetic acid (BP AMD) ([68Ga]BPAMD). In other embodiments, detecting the labeling agent includes Micro CT, Micro SPECT, and/or PET imaging. In other embodiments, detecting the labeling agent further includes comparison of the quantity of detected labeling agent with one or more control samples. In other embodiments, the method includes further culturing of MSCs, osteoblasts and/or osteocytes in the microfluidic device. In other embodiments, the method includes further detection of the labeling agent.

In various embodiments, the method includes applying one or more pulse sequences to the microfluidic device, and detecting the pulse sequence signal intensity, wherein the pulse sequence signal intensity is capable of measuring one or more biochemical properties. In other embodiments, detecting the pulse sequence signal intensity includes chemical exchange saturation transfer (CEST), pH measurement of Tl rho, magnetization transfer contrast (MTC), and/or magnetization exchange (MEX). In other embodiments, CEST detects a quantity of glycosaminoglycans (GAGs). In other embodiments, pH measurement of Tl rho detects a quantity of GAGs. In other embodiments, MTC detects a quantity of collagen. In other embodiments, MEX detects a quantity of collagen and/or osteoid. In other embodiments, the microfluidic device further includes one or more channels for loading of a control sample. In other embodiments, detecting the pulse sequence signal intensity further includes comparison of the quantity of detected labeling agent with one or more control samples. In other embodiments, the method includes further culturing of stem cells in the microfluidic device. In other embodiments, the method includes further culturing of cartilage, tendon/ligament, nucleus pulposus, annulus fibrosus, chondrocytes, tenocytes, fibroblasts, and/or notochordal cells among others. In other embodiments, the method includes further detection of pulse sequence signal intensity. In various embodiments, the method includes detecting cellular mineralization. In other embodiments, the method includes detecting secreted extracellular macromolecules. In various embodiments, the method includes detecting cellular survival, differentiation and/or proliferation.

Described herein is a method of detecting cellular mineralization in a microfluidic device including providing a microfluidic device including mesenchymal stem cells (MSCs), osteoblasts and/or osteocytes, adding one or more labeling agents to the microfluidic device, and detecting the labeling agent, wherein the labeling agent is capable of binding to cellular mineralization. In other embodiments, the microfluidic device further includes one or more channels for loading of a control sample. In other embodiments, the one or more labeling agents comprise bisphosphonate imaging agents. In other embodiments, the bisphosphonate imaging agent includes a pamidronate backbone with a fluorescent label. In other embodiments, the one or more labeling agents comprise a radiolabel. In other embodiments, the radiolabel includes technetium-99m ([99mTc]-BPs), [18F]-Fluoride, 99mTc-Methyl diphosphonate (Tc-MDP), and/or 68Ga-Labeled (4-{[(bis(phosphonomethyl))carbamoyl] methyl}-7,1 O-bis(carboxymethyl)-I,4, 7, I 0-tetraazacyclododec-1-yl)acetic acid (BP AMD) ([68Ga]BPAMD). In other embodiments, detecting the labeling agent includes Micro CT, Micro SPECT, and/or PET imaging. In other embodiments, detecting the labeling agent further includes comparison of the quantity of detected labeling agent with one or more control samples. In other embodiments, the method includes further culturing of MSCs, osteoblasts and/or osteocytes in the microfluidic device. In other embodiments, the method includes further culturing cartilage, tendon/ligament, nucleus pulposus, annulus fibrosus, chondrocytes, tenocytes, fibroblasts, and/or notochordal cells in the microfluidic device. In other embodiments, the method includes further detection of the labeling agent.

Also described herein is method of detecting secreted extracellular macromolecules in a microfluidic device including providing a microfluidic device including stem cells, applying one or more pulse sequences to the microfluidic device, and detecting the pulse sequence signal intensity, wherein the pulse sequence signal intensity is capable of measuring one or more macromolecules secreted by the stem cells. In other embodiments, the stem cells are mesenchymal stem cells (MSCs). In other embodiments, the stem cells are induced pluripotent stem cells (iPSCs). In other embodiments, detecting the pulse sequence signal intensity includes chemical exchange saturation transfer (CEST), pH measurement of Tl rho, magnetization transfer contrast (MTC), and/or magnetization exchange (MEX). In other embodiments, CEST detects a quantity of glycosaminoglycans (GAGs). In other embodiments, pH measurement of Tl rho detects a quantity of GAGs. In other embodiments, MTC detects a quantity of collagen. In other embodiments, MEX detects a quantity of collagen and/or osteoid. In other embodiments, the microfluidic device further includes one or more channels for loading of a control sample. In other embodiments, detecting the pulse sequence signal intensity further includes comparison of the quantity of detected pulse sequence signal intensity with one or more control samples. In other embodiments, the method includes further culturing of stem cells in the microfluidic device. In other embodiments, the method includes further culturing cartilage, tendon/ligament, nucleus pulposus, annulus fibrosus, chondrocytes, tenocytes, fibroblasts, and/or notochordal cells in the microfluidic device. In other embodiments, the method includes further detection of pulse sequence signal intensity.

In one embodiment, the invention provides a method of osteogenic differentiation comprising a) seeding mesenchymal stem cells (MSCs) on a laminin-coated porous flexible membrane in an microfluidic device in culture medium in the absence of Bone Morphogenetic Protein-2 (BMP2) and the absence of flow until the MSCs attach to the membrane, b) flowing the culture medium in the absence of BMP2 such that the MSCs proliferate to produce confluent MSCs, and c) contacting the confluent MSCs with osteogenic medium containing BMP2 to produce differentiated cells that express one or more osteogenic markers exemplified by, but not limited to, osteocalcin, bone sialoprotein (bsp), osteopontin (opn), and collagen type 1. (Examples 9-13 and FIGS. 5A-B-8A-E).

The invention's systems and methods have several advantages. The Bone-chip (exemplified in FIG. 5A-B) provides a platform for optical imaging of the cells and potentially biomechanical forces can be applied.[31,32] The cell response to those forces can be tested in vitro without the need to harvest them. Furthermore, the chips are composed of a membrane that may be coated covalently or non-covalently with any desired ECM components allowing recapitulation of cells natural environment. Additional prominent advantage is the ability to control and to manipulate the flow sensed by cells, which has a known effect on cell differentiation as shown in several models[33,34].

The invention's systems and methods additionally have the advantage that the optical imaging can be used not only for regenerative medicine oriented research, but also to metabolism research and to disease modeling by using any of the wide range of commercially available probes for hypoxia,[40] metabolism,[41] inflammation[42] and so on. The genetic tagging by the luciferase transgene can be used as a reporter to virtually any gene, including prokaryotic genes.[43]

The invention's systems and methods also have the advantage of being able to be further developed to mimic the regenerating bone in finer ways; the chip can be used to mimic the biomechanical shears forces that are often exerted on healing fracture, using vacuum channels created parallel to the main cell culture channels.[31] Different bone ECM components may be used. The flow can be used to introduce the system with chemokines that are known to play critical role in in-vivo fracture healing, such as TNF-alpha and IL-17,4 or systemically administrated osteogenic therapies such as Parathyroid hormone.[45,46] The outflow can be collected and analyzed for the cell secretome.[47] A refined design of the chip may evolve in to organoid-like 3D chip.[48] The invention's systems and methods may be used to study the relation of regenerating bone to adjacent tissues including tendon and cartilage. To sum, the invention's system and methods have a great potential to expedite the discovery and exploration of cutting edge approaches to bone tissue disease and regeneration, using methods of non-invasive imaging.

In one embodiment, the differentiated cells express a higher level of at least one of osteocalcin, bone sialoprotein (bsp), osteopontin (opn), and collagen type 1 compared to the MSCs. For example, gene expression and immunofluorescence data herein (Examples 11-13 and FIGS. 7A-F-8A-

E) show that all three Osteopontin (OPN), Collagen type 1 and Bone Sialoprotein (BSP) genes were elevated in the static culture to 1-2 times comparing to non-differentiating cells, while in the flow cultured cells the OPN expression was tripled, the BSP expression raised by factor 5 and the Collagen-1 expression was increased by factor 6 compared to non-differentiating MSCs. The immunofluorescence data (Example 13 and FIG. 4) also show increased expression of Osteocalcin, BSP, and Collagen type 1 compared to null expression in the control MSCs.

While not intending to limit the culture conditions, in one embodiment, the contacting step is in the presence of flow of the osteogenic medium. For example, data herein in Examples 12-13 and FIG. 8A-E show that all three Osteopontin (OPN), Collagen type 1 and Bone Sialoprotein (BSP) genes were elevated in the flow conditions, i.e., the OPN expression was tripled, the BSP expression raised by factor 5 and the Collagen-1 expression was increased by factor 6 compared to non-differentiating MSCs. In one embodiment, the contacting step is in the absence of flow of the osteogenic medium. For example, data herein in Examples 11-13 and FIGS. 7A-F-8A-E show osteogenic differentiation of the MSC-BMP2 cells in static conditions produced 1-2 times overexpression of Osteopontin (OPN), Collagen type 1 and Bone Sialoprotein (BSP) in all differentiated cells comparing to non-differentiating cells. In one embodiment, the differentiated cells express a higher level of at least one of osteocalcin, bone sialoprotein (bsp), osteopontin (opn), and collagen type 1 in the presence of flow of the osteogenic medium compared to in the absence of flow of the osteogenic medium (Examples 11-13 and FIGS. 7A-F-8A-E).

Without intending to limit the type or nature of the components in the osteogenic medium, in one embodiment, the osteogenic medium contains β-glycerophosphate and L-Ascorbic acid. Data in Example 9 shows the exemplary use of a combination of 10 mM β-glycerophosphate, 50 μg L-Ascorbic acid. In one embodiment, the β-glycerophosphate concentration may range from 0.1 mM to 1.0 M, including from 0.1 mM to 1 mM, 0.1 mM to 10 mM, and 0.1 mM to 100 mM. In one embodiment, the L-Ascorbic acid amount may range from 1 μg to 10 μg, 1 μg to 50 μg, 1 μg to 100 μg, 1 μg to 500 μg, 1 μg to 1 mg, and 1 μg to 5 mg.

While not intending to limit the invention's methods to a particular method of determining the status of cells in the microfluidic device, in one embodiment, the method comprises non-invasive determination of one or more of the survival status, proliferation status, and differentiation status of the MSCs and/or differentiated cells in the microfluidic device (Examples 9-13).

Data herein (Examples 9-13) demonstrate the development of a Bone-Chip for determining osteogenic differentiation in-vitro, coupled with a novel optical imaging approach which addresses the prior art's limitations while allowing the application of biomechanical forces.

Data herein (Examples 9-13) demonstrate that optical imaging can be utilized to non-invasively monitor stem cell survival and differentiation while cultured in an "organ-on-chip" device. Furthermore, the data demonstrate that the micro-engineered environment within the Bone-Chip promotes cell proliferation and more efficient osteogenic differentiation and that optical imaging can be utilized to non-invasively monitor stem cell survival and differentiation while cultured in an "Organ-on-Chip" system.

Data herein (Examples 9-13) demonstrate that optical imaging can be utilized to non-invasively monitor stem cell survival and differentiation while cultured in an "Organ-on-Chip" system, and that the micro-engineered environment within the Bone-Chip promotes cell proliferation and more efficient osteogenic differentiation. The invention was exemplified herein (Examples 9-13) using Mesenchymal Stem Cell (MSC) line over-expressing Bone Morphogenetic Protein-2 (BMP-2) under Tet-Off system and Luciferase reporter gene under constitutive promoter, that were seeded on laminin coated Chips and supplemented with osteogenic medium. Flow of media was started 24 hours after seeding, while static cultures were performed using media reservoirs. The invention's methods provide an improvement over prior methods in which it was shown that microfluidic flow can be used to pattern osteogenic differentiation of MSC bearing the Tet-off-BMP-2, by patterning the delivery of BMP-2 modulator doxycycline[35], although osteogenesis was demonstrated only by using imaging techniques that require termination of the culture—ALP and Von Kossa stainings, calcium deposition measurement and immunohistochemistry against Bone-sialoprotein.

Data herein (Examples 9-13) demonstrate cell survival/proliferation of cells grown on the Bone-Chips under constant flow of media was enhanced comparing to the cells grown in static conditions; Luciferase reporter gene expression and activity, reflecting the cell survival and proliferation, was quantified using bioluminescence imaging twice a week and significant advantage to the flow system was observed. Also, the micro-engineered environment with flow had positive effect on osteogenic differentiation, when compared with static cultures. Fluorescent imaging was performed using the osteogenic ECM-targeted probes OsteoSense[650] and BoneTag[800], followed by quantification which showed higher osteogenic differentiation of the cells under the flow conditions. Gene expression analysis confirmed the osteogenic differentiation of the MSC-BMP2 cells, showing upregulation of Osteopontin, Collagen type 1 and Bone Sialoprotein (BSP) in all cells, yet higher expression was observed in the cells cultured in flow conditions. Immunofluorescent staining performed against the Osteocalcin, Col1, and BSP markers on transverse sections across the channels or whole Bone-Chips illustrated robust osteogenesis in the flow culture and lessened differentiation in the static culture. To sum, the Bone-Chip allows monitoring cell survival, proliferation and osteogenic differentiation in-vitro using optical imaging, without the need for sacrificing the Chips enabling additional endpoints or culture time.

More particularly, data herein (Examples 9-13) focused on the longitudinal non-terminal imaging of a "Bone-on-a-chip" system. For this purpose, a differentiating system that includes Mesenchymal Stem Cells (MSCs) over-expressing of Bone Morphogenetic Protein-2 (BMP-2) was utilized[23-25]. The recombinant BMP-2 protein is FDA-approved and in wide use in the clinical settings using a very high dose which quickly deteriorates, while different experimental systems offer sustained expression of a milder dose for as long as 14 days using non-viral gene delivery[26], or for the cell life time in case of MSCs transfected with lentivirus. BMP-2 affects MSC via both by paracrine and autocrine signaling, that are transduced to the nucleus via secondary messengers including the Smad family which enhance the expression of osteogenic transcription factors such as RUNX2, Osterix and others[27]. To allow a controllable expression of BMP-2 in MSC, the invention used the exemplary Tetracycline-off system[23], that was successfully examined in a various of clinically relevant models including spinal fusion[28], long-bone allograft regeneration[29], radial defects[30], and more.

Figure 6A:
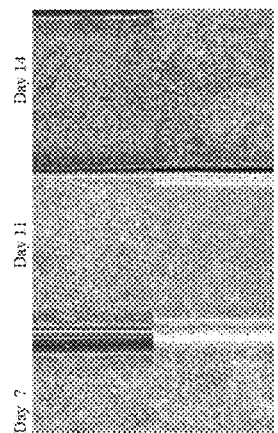
FIG. 6A-C. Cell survival and proliferation on the Bone-Chip. Micrographs of the cells in the Bone-Chip grown for 2 weeks were taken biweekly, in osteogenic conditions with or without flow.
Figure 6B:
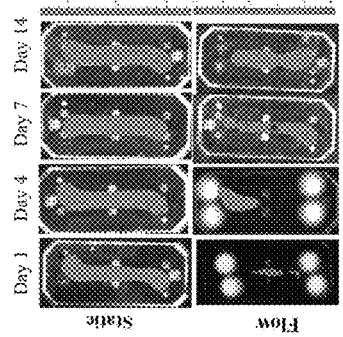
Figure 6C:
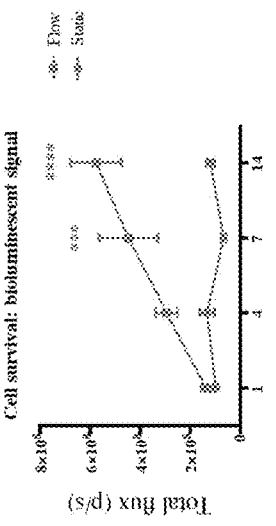

Data herein demonstrate that BLI of cells continuously expressing the luciferase gene can faithfully reflect cell proliferation, and detect superior proliferation when it was present under the flow conditions (FIG. 6A-C). Next, FLI and a targeted molecular probe were used to allow detection of osteogenic differentiation, signified by osteogenic ECM secretion (FIG. 7A-F). Data herein show that the osteoid-targeted OsteoSense$^{650}$ probe provided the ability to monitor osteogenesis and even discern more rigorous differentiation comparing to moderate differentiation, as confirmed by gene expression analysis and immunofluorescence (FIG. 8A-E). The BoneTag800 which serves as a calcium chelator could not be used to produce meaningful data, yet it might be used for cultures sustained for longer periods when the culture is expected to mature. Another interesting observation was that the IVIS system, originally designated to rodent imaging, could detect the differentiation towards the osteoblastic lineage but did not contribute to the characterization of which. Only the combined used of the IVIS system and the NIR imager, conceived to read out smaller samples such as western blot gels, has assembled a finer image of the differentiation process. Thus, data herein show that the IVIS can be used in invention's system to answer a yes/no question: is there any differentiation? While the NIR imager can be used to answer a more delicate question: what's the extent of the desired differentiation?Organ-on-chip system allows monitoring of the cell survival and proliferation in vitro using BLI imaging system and monitor the osteogenic differentiation of the cell on the chip in real time, without the need of harvesting the cells and disrupting the culture conditions. Here, the Inventors demonstrate that the flow conditions affect both proliferation and the differentiation of the MSCs that overexpress BMP2.

I. Open-top Microfluidic devices.

The invention contemplates fluidic devices comprising one or more osteogenic cell types. Accordingly, the present invention contemplates the use of open-top microfluidic devices, exemplified in FIGS. 10-12A-B. Open-top microfluidic devices include but are not limited to microfluidic devices having removable covers, such as removable plastic covers, paraffin covers, tape covers, etc.

Many of the problems associated with earlier systems can be solved by providing an open-top style microfluidic device that allows topical access to one or more parts of the device or cells that it comprises. For example, the microfluidic device can include a removable cover, that when removed, provides access to the cells of interest in the microfluidic device. In some aspects, the microfluidic devices include systems that constrain fluids, cells, or biological components to desired area(s). The improved systems provide for more versatile manipulations using microfluidic devices, including improved application of treatments being tested, improved seeding of additional cells, and/or improved aerosol delivery for select tissue types.

Therefore, in one embodiment, the present invention contemplates using a microfluidic device with an opening that provides direct access to device regions or components (e.g. access to a 2D or 3D matrix (such as 2D or 3D extracellular matrix) containing cultured and/or differentiated cells, access to one or more cellular components, etc.). Although FIGS. 10-12A-B provide an embodiment wherein the opening is at the top of the device (referred to herein with the term "open-top"), the present invention contemplates other embodiments where the opening is in another position on the device. For example, in one embodiment, the opening is on the bottom of the device. In another embodiment, the opening is on one or more of the sides of the device. In another embodiment, there is a combination of openings (e.g. top and sides, top and bottom, bottom and side, etc.).

While detailed discussion of the "open-top" embodiment is provided herein, those of ordinary skill in the art will appreciate that many aspects of the "open-top" embodiment apply similarly to open bottom embodiments, as well as open side embodiments or embodiments with openings in any other regions or directions, or combinations thereof. Similarly, the device need not remain "open" throughout its use; rather, as several embodiments described herein illustrate, the device may further comprise a cover or seal, which may be affixed reversibly or irreversibly. For example, removal of a removable cover creates an opening, while placement of the cover back on the device closes the device. The opening, and in particular the opening at the top, provides a number of advantages, for example, allowing (i) the creation of one or more 3D ECM layers for simulating the application of topical treatments on the cells, tissues, or organs, or (ii) the addition of chemical or biological components such as the seeding of additional cell types for simulated tissue and organ systems.

The present invention contemplates a variety of uses for these open-top microfluidic devices and methods described herein. In one embodiment, the present invention contemplates a method of topically administering an agent (whether a drug, food, gas, or other substance) comprising 1) providing a) an agent and b) microfluidic device comprising i) a chamber, said chamber comprising a lumen and projections into the lumen, said lumen comprising ii) a 3D matrix (in some embodiments a 3D ECM) anchored by said projections and comprising cell in, on or under said 3D matrix, said matrix positioned above iii) a porous membrane and under iv) a removable cover, said membrane in contact with v) fluidic channels; 2) removing said removable cover; and 3) topically contacting said cells in, on or under said matrix with said agent. These uses may apply to the open-top microfluidic devices described below and herein.

A. Open-Top Microfluidic Devices Without Extracellular Matrix (ECM).

In one embodiment, open-top microfluidic devices do not contain ECM, either as a 3D ECM or a 2D ECM layer. Thus, the present invention also contemplates, in one embodiment, a layered structure comprising i) fluidic channels covered by ii) a porous membrane, said membrane comprising iii) a layer of cells and said membrane positioned below said cells. In one embodiment, there is a removable cover over the cells.

Additional embodiments are described herein that may be incorporated into open-top microfluidic devices without a three dimensional matrix such as an extracellular matrix (3D ECM)s.

B. Open-Top Microfluidic Devices with Extracellular Matrix (ECM).

In one embodiment, open-top microfluidic devices contain a matrix such as an ECM, as a 2D or 3D layer. In one embodiment, the open-top microfluidic device has an open-top region that reduces the impact of stress that can cause the delamination of tissue or related component(s) (e.g., such as a three dimensional extracellular matrix (3D ECM)). Thus, in one embodiment, the open-top microfluidic device comprises a matrix including, but not limited to a 3D ECM. In one embodiment, the open-top microfluidic device does not contain a 3D ECM.

The present invention also contemplates, in one embodiment, a layered structure comprising i) fluidic channels covered by ii) a porous membrane, said membrane comprising iii) a layer of cells and said membrane positioned below iv) a 3D ECM. In one embodiment, there is a removable cover over the 3D ECM (and/or cells). It is not intended that the present invention be limited to embodiments with only one 3D ECM. In one embodiment, the layered structure further comprises a second 3D ECM (e.g. positioned under said membrane). The 3D ECM(s) or coatings can be patterned or not patterned. Moreover, when patterned, the pattern need not extend to the entire surface. For example, in one embodiment, at least a portion of said 3D ECM is patterned. It is not intended that the present invention be limited by the nature or components of the 3D ECM or ECM coating. A variety of thickness is contemplated. In one embodiment of the layered structure, said 3D ECM is between 0.2 and 6 mm in thickness.

Figure 10:
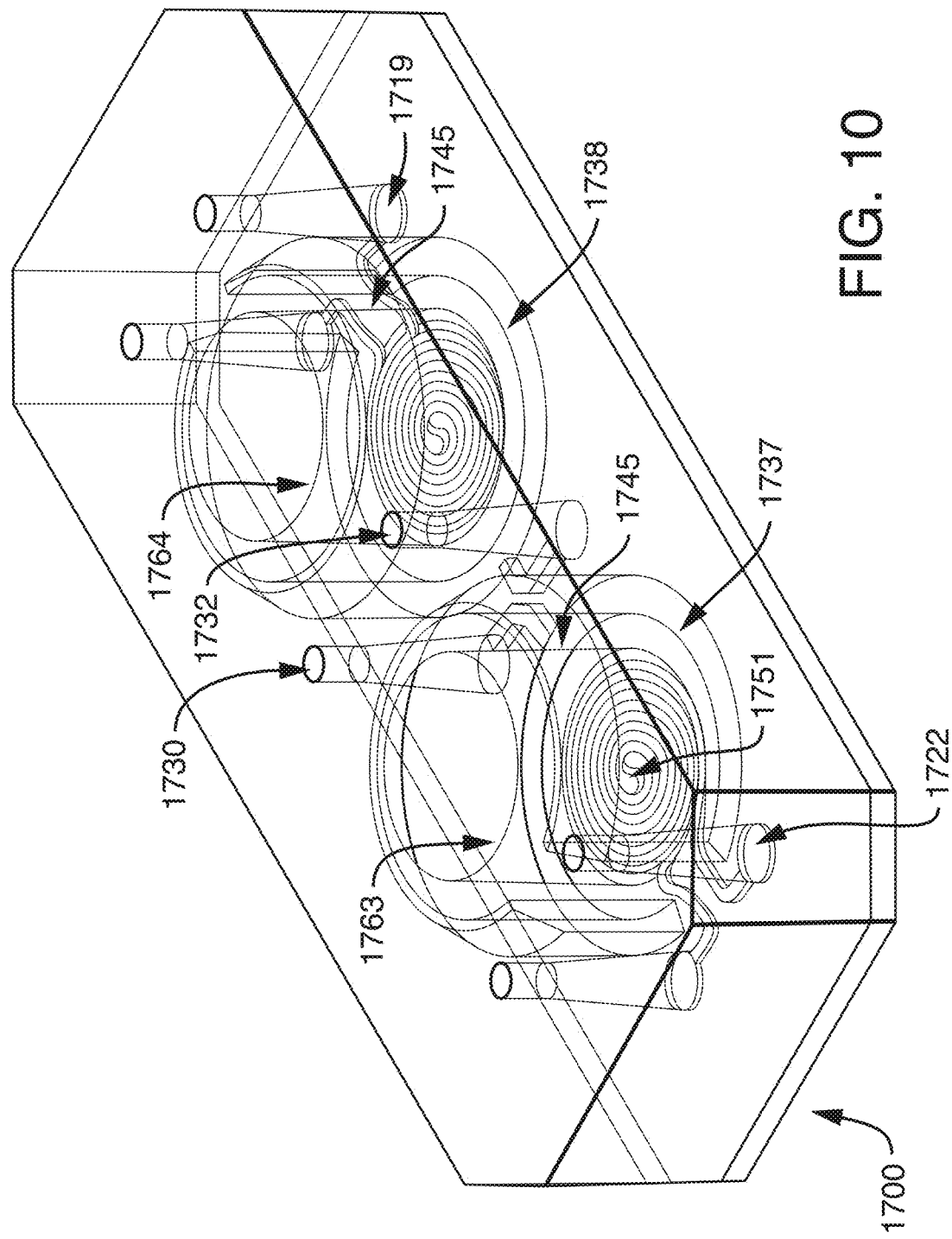
FIG. 10 shows one embodiment of an assembled microfluidic device, showing the open-top chambers above the fluidics.
Figure 11:
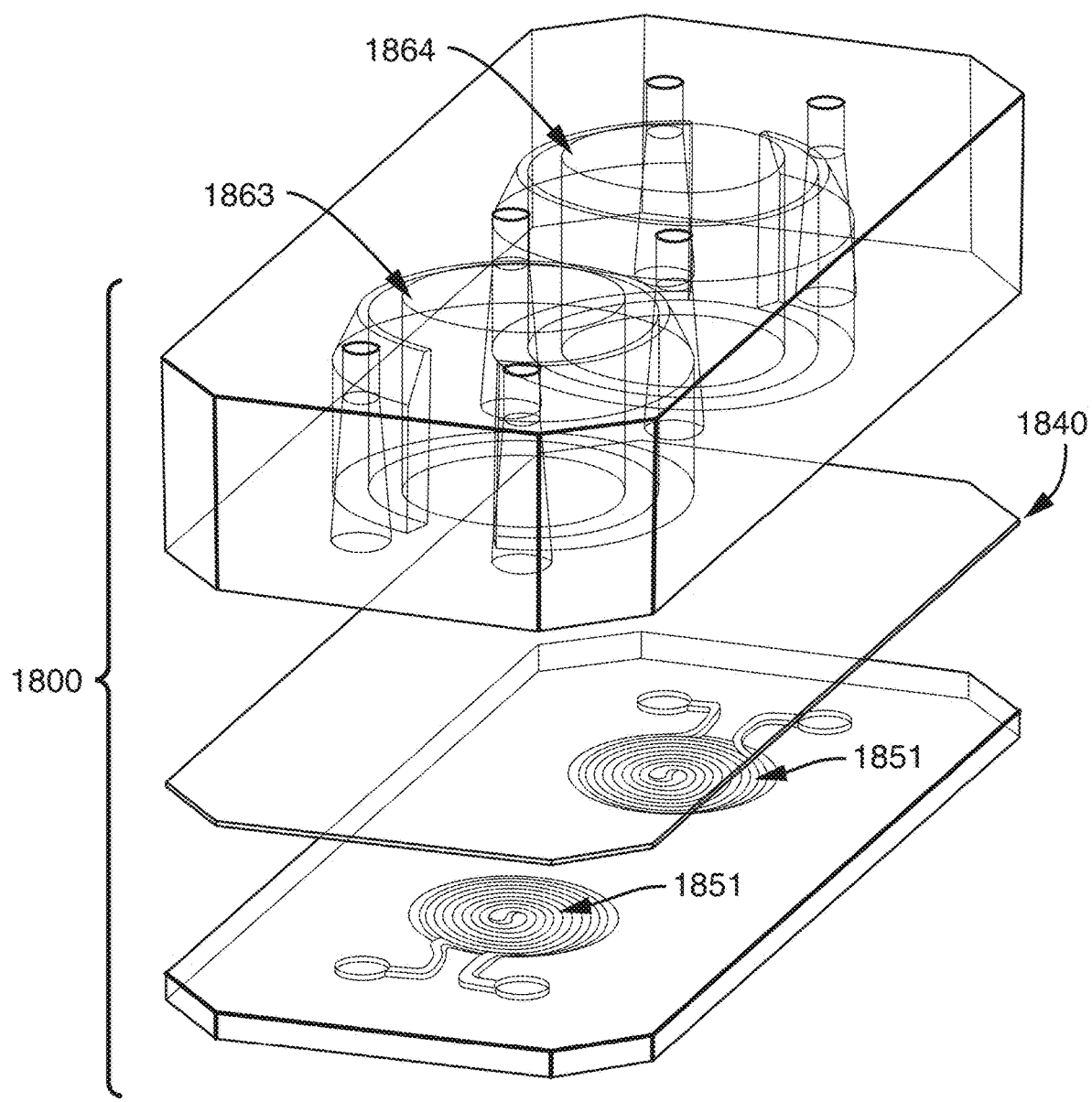
FIG. 11 shows the embodiment of FIG. 10, wherein the membrane is highlighted in order to illustrate the relationship of the assembled components.

In one embodiment, the present invention contemplates an open-top microfluidic device, exemplified by those described in WO2017096297, published Jun. 8, 2017, incorporated herein by reference. For example, in one embodiment exemplified in FIGS. 10-11, the present invention contemplates an open-top microfluidic device 1700 comprising: i) a first chamber 1763 and a second chamber 1764, wherein each chamber is surrounded by a deformable surface 1745; and ii) at least two spiral microchannels 1751 located on the bottom surface of the chambers, wherein each of the microchannels are in fluidic communication with an inlet port 1719 and an outlet port 1722 and are respectively configured with a first vacuum port 1730 or a second vacuum port 1732, such that each vacuum port is respectively connected to a first vacuum chamber 1737 or a second vacuum chamber 1738. An exploded view of the embodiment depicted FIG. 10 shows an open-top microfluidic device 1800, wherein a membrane 1840 resides between the bottom surface of the first chamber 1863 and the second chamber 1864 and the at least two spiral microchannels 1851. FIG. 11.

Figure 12B:
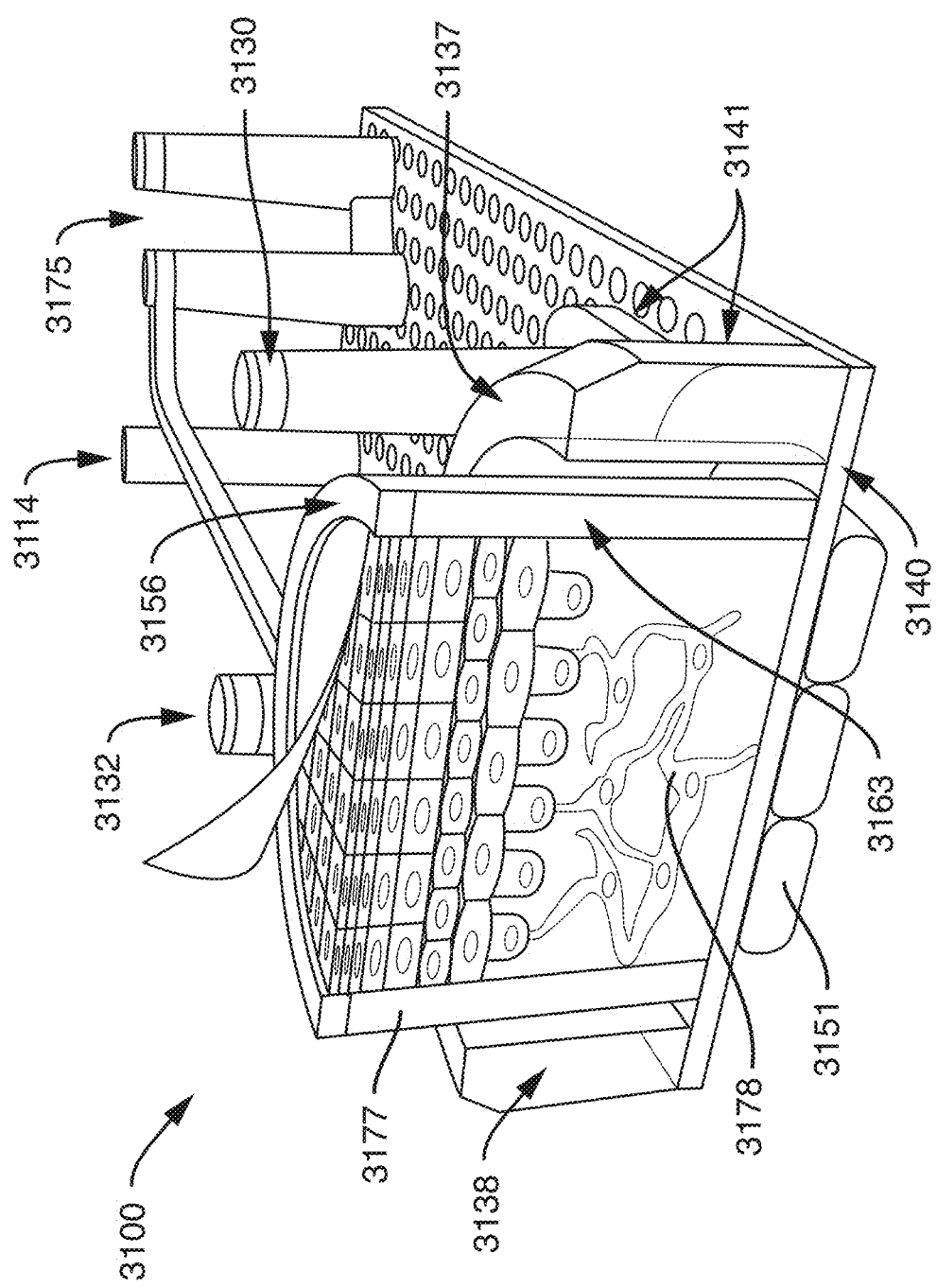
Figure 13:
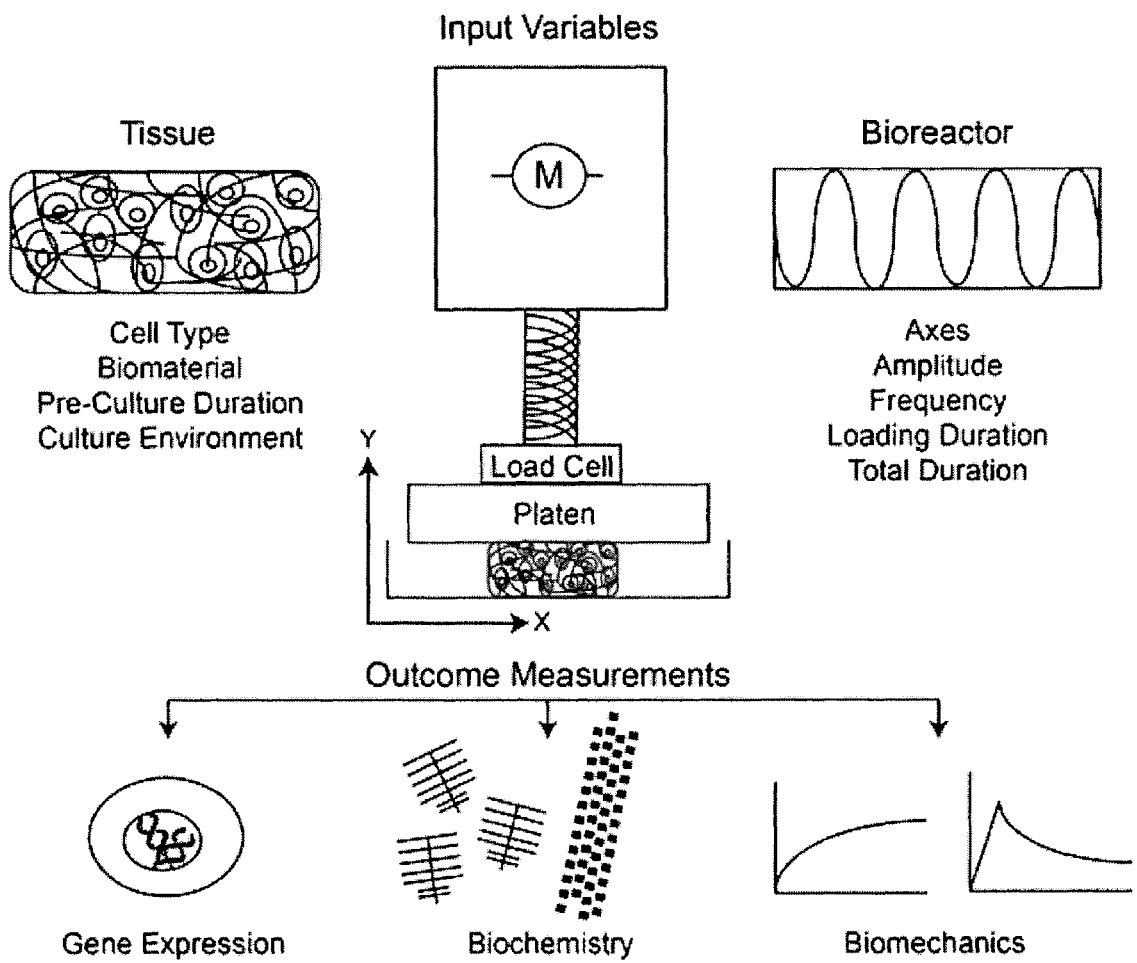
FIG. 13. Schematic of the input variables and outcome measurements under consideration in study design, and interpretation thereof, for dynamic compression of cells.

In another example, in one embodiment exemplified in FIG. 12A-B, the present invention contemplates a stretchable open-top microfluidic device 3100 comprising a chamber 3163 comprising a first region 3177 and a second region 3178. In one embodiment, the first region comprises a first cell layer (e.g., MSCs, osteoblast lineage cell types, epithelial cells, dermal cells and/or endothelial cells). In one embodiment, the second region comprises a second cell layer (e.g., MSCs, osteoblast lineage cell types, epithelial cells, dermal cells and/or endothelial cells), wherein said first cell layer adheres to the surface of the second cell layer. In one embodiment, the cell type in the first cell layer and in the second cell layer is different (e.g., MSC in the first cell layer and endothelial cell in the second cell layer. In one embodiment, the device further comprises a spiral microchannel 3151 in fluid communication with a fluid inlet port 3114, wherein the microchannel comprises a plurality of endothelial cells. In one embodiment, a membrane 3140 is placed between the chamber second cell layer and the microchannel plurality of endothelial cells. In one embodiment, the device further comprises an upper microchannel with a circular chamber 3156 connected to a fluid or gas port pair 3175. In one embodiment, the device further comprises a first vacuum port 3130 connected to a first vacuum chamber 3137 and a second vacuum port 3132 connected to a second vacuum chamber 3138. In one embodiment, the membrane 3140 comprises a PDMS membrane comprising a plurality of pores 3141, wherein said pores 3141 are approximately 50 µm thick, approximately 7 µm in diameter, packed as 40 µm hexagons, wherein each pore has a surface area of approximately 0.32 cm2. Although it is not necessary to understand the mechanism of an invention, it is believed that the pore surface area contacts a gel layer (if present). FIGS. 12 A and 12 B.

II. Mechanical Stimulation

The invention contemplates applying mechanical stimulation to one or more cell types in the microfluidic device as exemplified in FIGS. 14-18.

Figure 14:
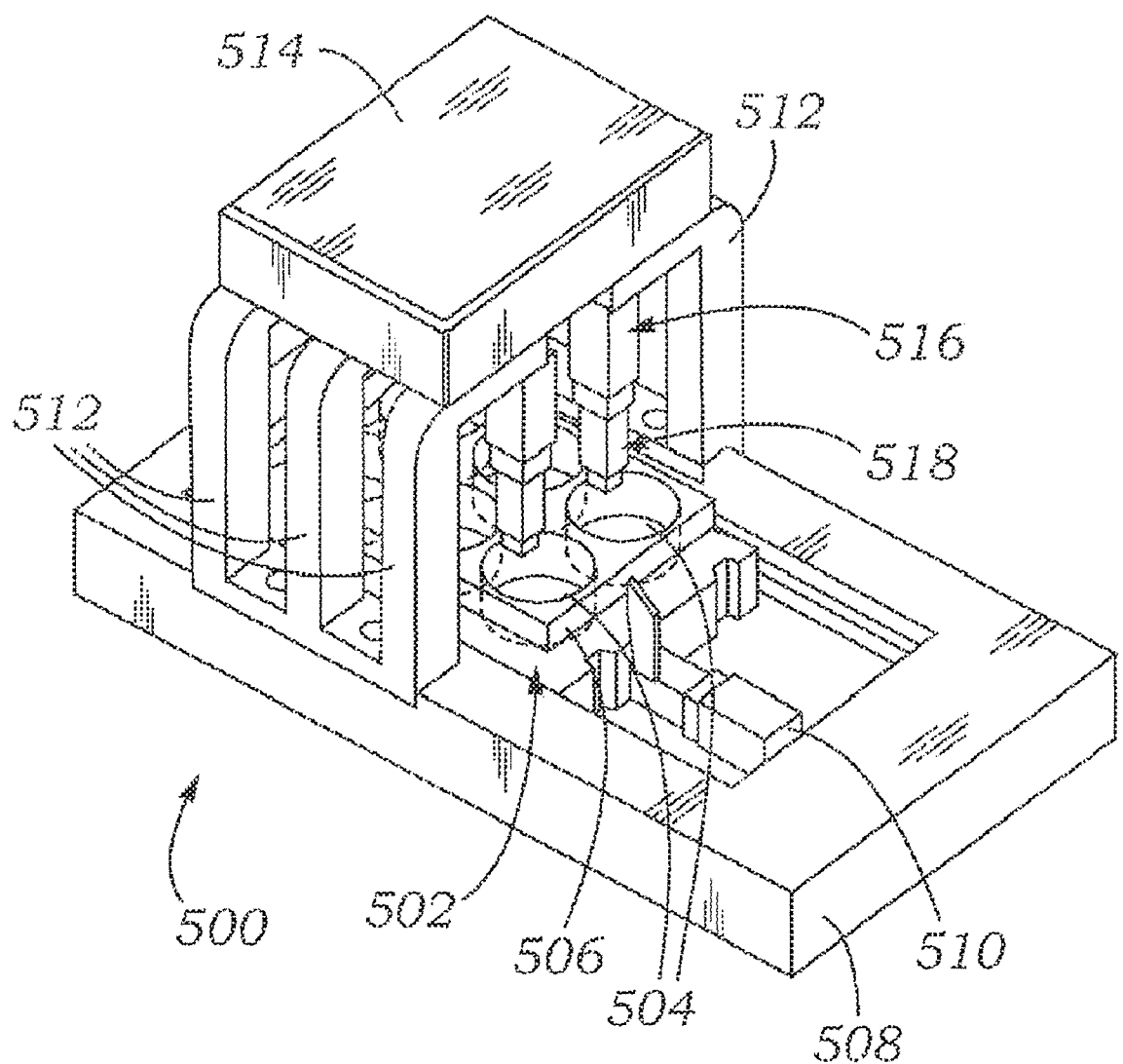
FIG. 14 shows a schematic drawing of an exemplary system having a plurality of mechanical actuators capable of mechanically stressing tissues within bioreactors or laboratory plates (Tuan et al. U.S. Pat. Application No. 20160201037, incorporated by reference).

FIG. 14 shows an exemplary system 500 comprising an array 502 of six bioreactors 504, which can have various configurations but in one specific embodiment can be similar to the bioreactor 100. The array 502 can be situated on a mount 506 which can be horizontally slidable relative to a base plate 508. The mount 506 can be actuated to move horizontally relative to the base plate 508 using a sliding actuator 510. The system 500 also includes a set of vertical extension arms 512 rigidly coupled to the base plate 508, and an actuator housing 514 rigidly coupled to the extension arms 512. The actuator housing 514 houses six micromechanical actuators 516, which can be used to impart forces to the bioreactors 504. The actuators 516 can also include force sensors 518 to monitor the force being imparted to ensure that sufficient, but not excessive, force is imparted to the bioreactors 504 and the tissues grown therein.

The system 500 can be modified to allow the six actuators 516 to mechanically stress more than six bioreactors 504. For example, additional bioreactors 504 can be situated on the mount 506 and can be moved under the actuators 516 by action of the sliding actuator 510. Thus, the actuators 516 can be used to sequentially stress tissues in a larger number of bioreactors. In other embodiments, a second sliding actuator can be used to make the mount 506 slidable along two perpendicular axes. Thus, the actuators 116 can be used to induce stresses in tissues in bioreactors of an array having a larger number of bioreactors 504 in two dimensions.

Figure 15:
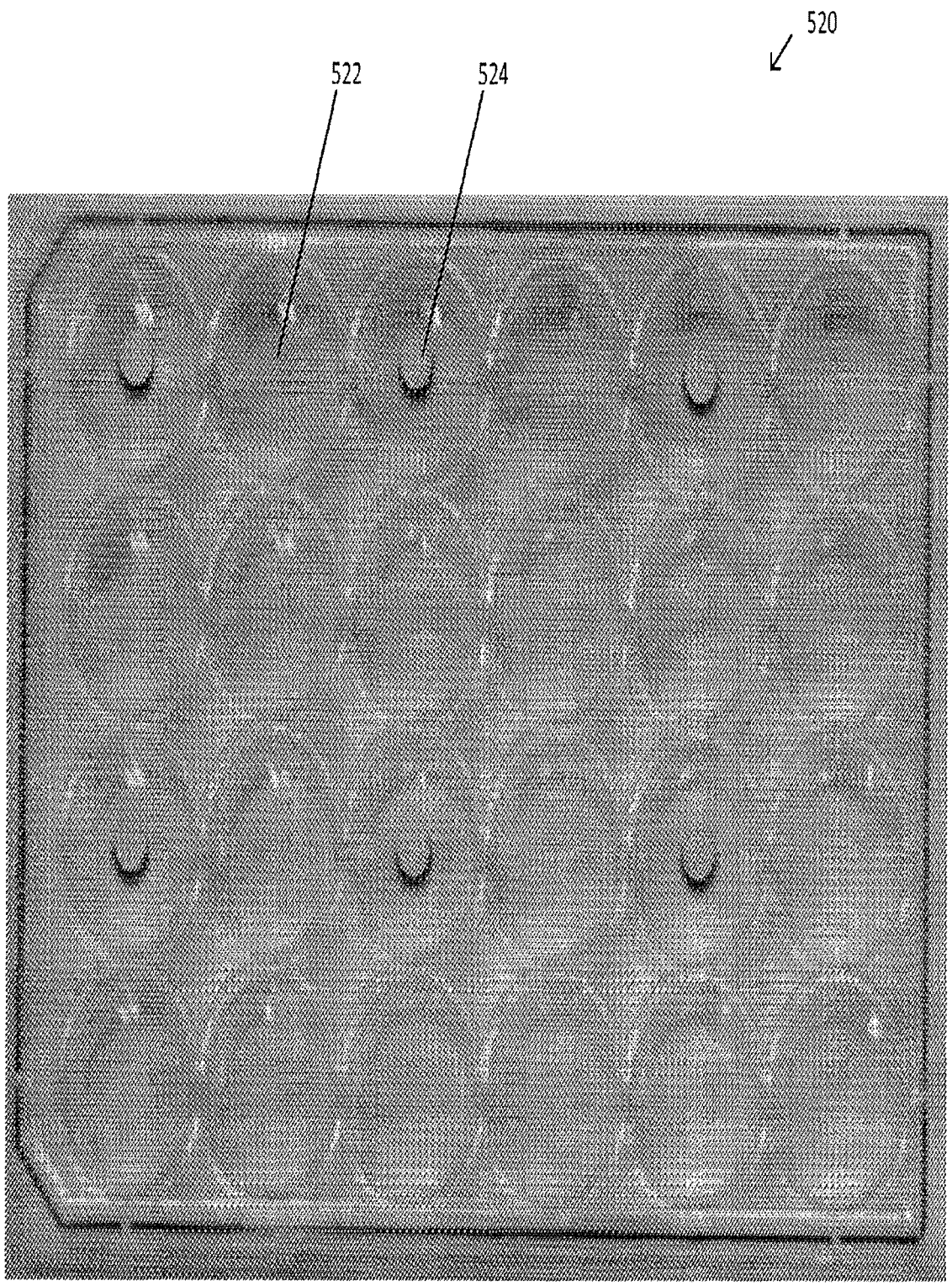
FIG. 15 illustrates an exemplary method of imparting an array of bioreactors with loading forces in groups of six at a time (Tuan et al. U.S. Pat. Application No. 20160201037, incorporated by reference).

FIG. 15 illustrates an exemplary method in which a multi-well tray of bioreactors can be sequentially stressed with loading forces in groups. For example, the tray 520 contains 24 bioreactors in a 4-by-6 array of wells 522. A mechanical loading apparatus, similar to that described in FIG. 14, can apply loading forces to groups of six of the bioreactors at a time. An exemplary group of six is represented by the six dots 524. After providing loading forces on the group of six represented by the dots 524, the tray 520 and/or the loading mechanism can be shifted such that a different group of six wells 522 and bioreactors is positioned below the six loading members of the loading mechanism. This can be repeated until all 24 bioreactors are imparted with loading forces. In this way, the total of 24 bioreactors can be imparted with loads in four sessions, with six bioreactors being imparted with loading forces in each of the four sessions. FIG. 15 illustrates just one exemplary loading pattern. In other loading patterns, groups of different numbers and/or arrangements of bioreactors can be included in each loading session.

Figure 16:
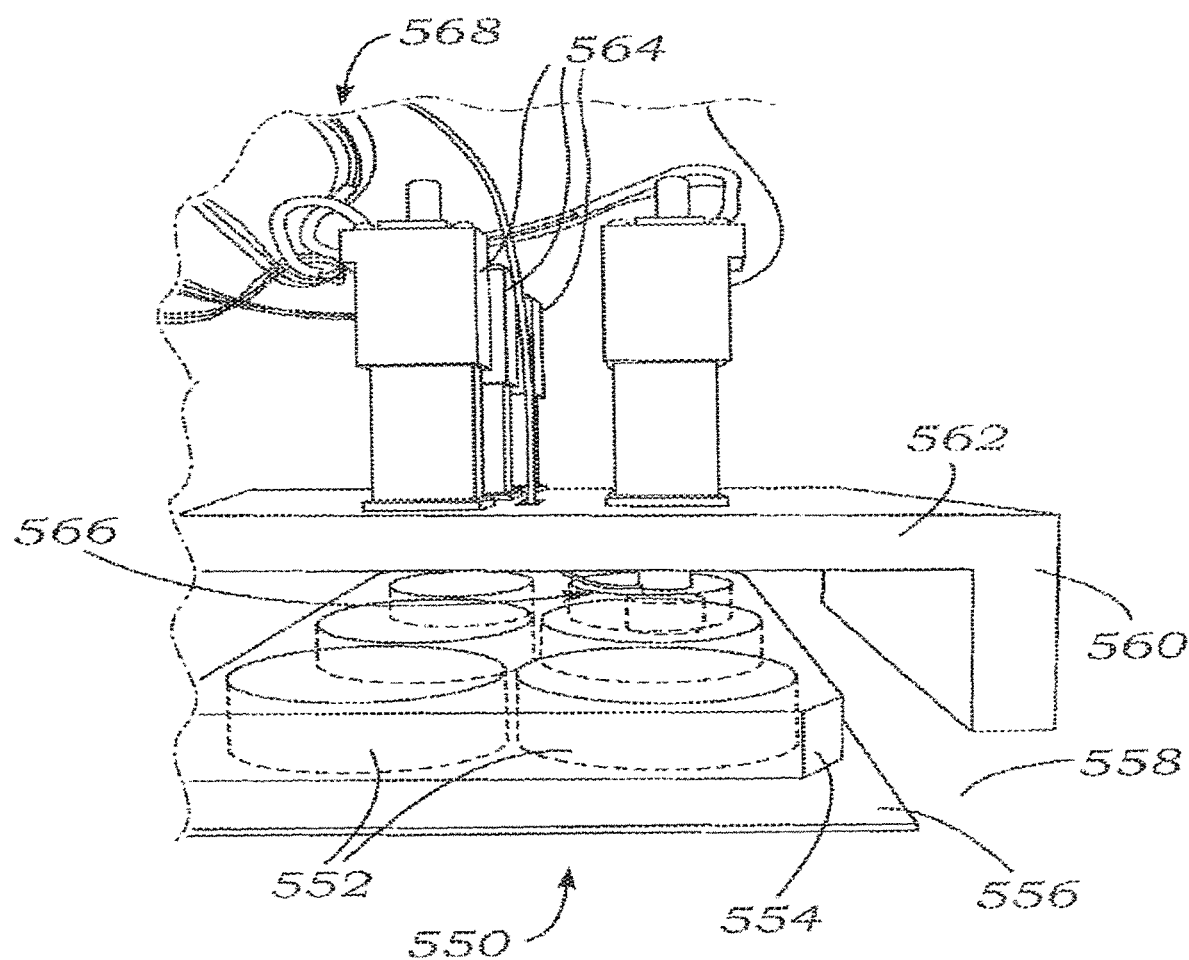
FIG. 16 shows a photograph of another exemplary system having a plurality of mechanical actuators capable of mechanically activating/stressing tissues grown in bioreactors and measuring their mechanical properties (Tuan et al. U.S. Pat. Application No. 20160201037, incorporated by reference).

FIG. 16 shows a side view of an exemplary system 550 comprising six bioreactors 552 housed in a container 554, the container 554 situated on a tray 556 resting on a rigid surface 558. FIG. 16 also shows that supports 560, resting on the rigid surface 558, support an actuator support platform 562, on which six micromechanical actuators 564 are mounted. As in system 500, system 550 can be used to mechanically stress tissues grown in the six bioreactors 552 situated below the actuators 564. As in system 500, force sensors 566 can be coupled to the actuators 564 to measure the forces imparted by the actuators, to ensure sufficient, but not excessive, force is imparted to the tissues in the bioreactors 552. Wiring 568 can be used to couple the actuators to a controller unit such as a computer (not shown). The controller unit can be used to control the forces exerted by the actuators and to monitor force readings from the force sensors 566.

Figure 17:
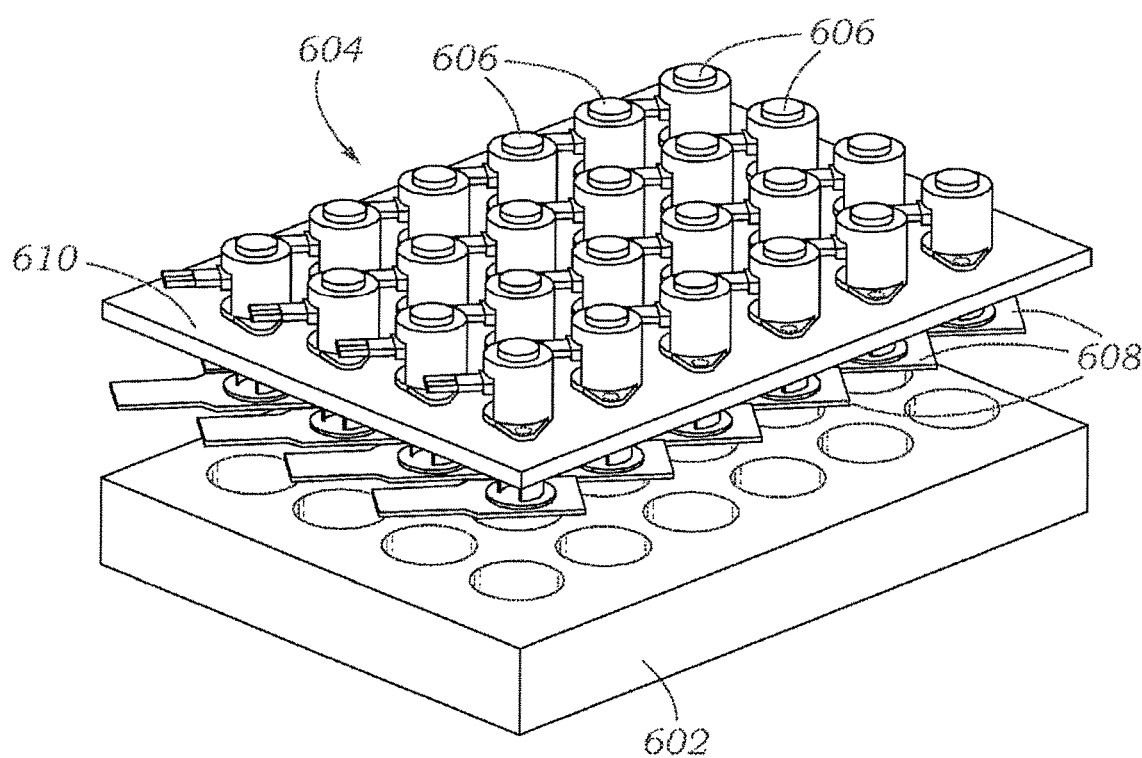
FIG. 17 shows a schematic drawing of another exemplary system having a plurality of mechanical actuators capable of mechanically activating/stressing tissues within laboratory multiwell plates and measuring their mechanical properties (Tuan et al. U.S. Pat. Application No. 20160201037, incorporated by reference).

FIG. 17 shows another exemplary system 600 including a twenty-four well plate 602 and a mechanical stimulator lid assembly 604. The well plate 602 comprises twenty four wells, within each of which a bioreactor (e.g., bioreactor 100) can be situated. An inner body (e.g., an inner body similar to inner body 116) having a protruding ring and being configured to be situated within a well of the well plate 602 can have at least one vertical channel formed in its protruding ring, which channel can be configured to accommodate a pipe or tube which can carry fluid from the lower chamber of a first bioreactor, over the wall between adjacent wells of the well plate 602, and to the lower chamber of a second bioreactor adjacent to the first bioreactor. The mechanical stimulator lid assembly 604 comprises twenty-four micromechanical actuators 606 and twenty-four respective force sensors 608 with associated pistons. The actuators 606 and the sensors 608 are mounted on a support plate 610. As in previous embodiments, the actuators 606 can be used to mechanically stress tissue growing in bioreactors situated in the wells of the well plate 602.

Figure 18:
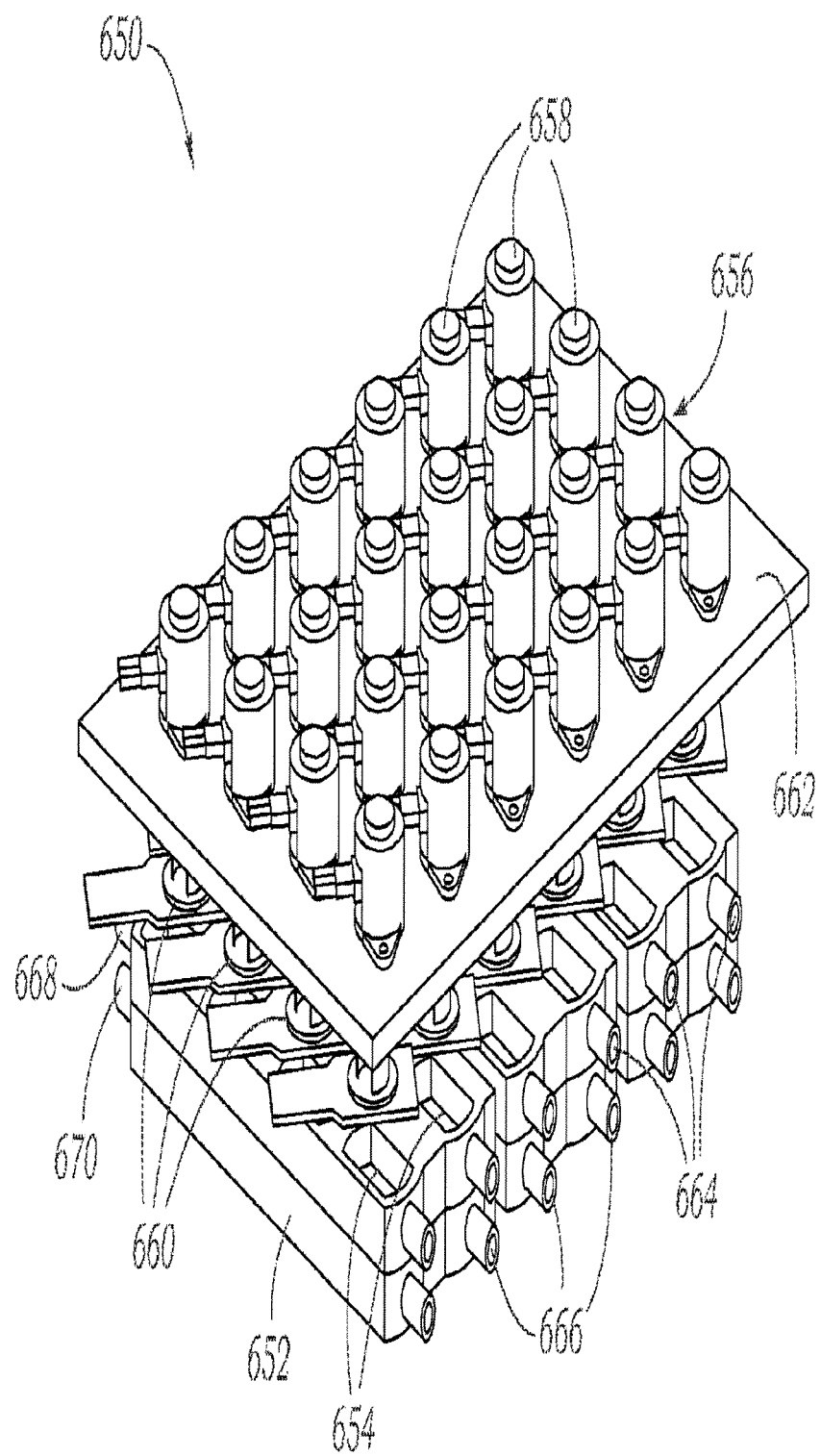
FIG. 18 shows a schematic drawing of another exemplary system having a plurality of mechanical actuators capable of mechanically activating/stressing tissues within bioreactors and measuring their mechanical properties (Tuan et al. U.S. Pat. Application No. 20160201037, incorporated by reference).

FIG. 18 shows another exemplary system 650 similar to system 600. System 650 includes a twenty four well plate 652 comprising twenty-four wells 654, and a mechanical stimulator lid assembly 656 comprising twenty four micromechanical actuators 658 and twenty-four force sensors 660 mounted on a support plate 662. Additionally, FIG. 11 shows upper inlets 664, lower inlets 666, upper outlet 668, and lower outlet 670.

The various methods and techniques described herein provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed herein, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are sources of mesenchymal stem cells, osteoblasts, bone cells or stem cells, seeding and culturing on a microfluidic device, imaging methods, including labeling and detection, and the particular use of the products created through the teachings of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the herein-described elements in all possible variations thereof is encompassed by the invention unless otherwise indicated herein or otherwise clearly contradicted by context.

Furthermore, numerous references have been made to patents and printed publications throughout this specification. Each of the references and printed publications cited herein are herein individually incorporated by reference in their entirety.

It is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

Example 1

Micro Imaging for Non Invasive Monitoring of Stem Cell-Induced Mineralization Mesenchymal stem cells (MSCs) can differentiate to various skeletal cells including osteoblasts. A common assay of MSC differentiation to osteogenic cells includes measurements of mineralization within the culture. Several methods can be used to monitor mineralization over time in chips

Example 2

Labeling Agents for Stem Cell-Induced Mineralization

Fluorescence imaging—bisphosphonate imaging probes such as OsteoSense™ (Perkin Elmer) can be added to the chip at different time points, washed and then the chip is imaged in an optical scanner. Hydroxyapatite (HA) is a mineral form of calcium apatite and is the major mineral product of osteoblasts. Therefore, HA levels are a good biomarker for osteoblast activity. In addition, abnormal accumulation of HA can be indicative of a disease state. OsteoSense™ imaging agents bind with high affinity to HA. Since hydroxyapatite (HA) is known to bind pyrophosphonates and phosphonates as well as synthetic bisphosphonates with high affinity, OsteoSense™ agents were designed as bisphosphonate imaging agents. These probes consist of a pamidronate backbone functionalized with near-infrared fluorophore off the amino terminus of the R2 side chain. Specifically, OsteoSense™ imaging agents can be used to image areas of microcalcifications, bone remodeling and enables imaging of bone growth and resorption. The bisphosphonate probe attaches to micro calcifications and the fluorescent readout provides quantification of mineralization.

Example 3

Other Labeling Agents for Stem Cell-Induced Mineralization

Bisphosphonates (BPs; also known as diphosphonates), such as methylene diphosphonate (MDP) and zoledronic acid, can be labeled with technetium-99m ([99mTc]-BPs) for use in bone scintigraphy as has been used to detect osteoporosis and other skeletal-related events (SREs). These chemicals bind hydroxyapatite, which allow for imaging of bisphosphonates as described above. [18F]-Fluoride is another nuclide that is commonly used for bone imaging, and positron emission tomography (PET) and is believed to be superior to [99mTc]-BPs for the diagnosis of SREs.

Micro SPECT/PET imaging-99mTc-Methyl diphosphonate (Tc-MDP) can be added to the chip at different time points, washed and then the chip is imaged using a micro SPECT scanner. Alternative probes are ['8F)-Fluoride or 68Ga-Labeled (4-{[(bis(phosphonomethyl))carbamoyl] methyl}-7,1 O-bis(carboxymethyl)-I,4, 7, I 0-tetraazacy-clododec-1-yl)acetic acid (BPAMD) [68Ga]BPAMD that can be imaged using a micro PET scanner. These probes also attach to mineralization foci and the uptake readouts can provide quantitative data of mineralization.

Example 4

Micro Imaging for Non Invasive Monitoring of Stem Cell-Induced Mineralization Micro CT—high-resolution micro CT scanners can detect mineral particles as small as 500 nm. A non-destructive scan of the chip can provide an accurate measurement of mineralization generated by the developing tissues.

Example 5

Micro Imaging for Non Invasive Monitoring of Extracellular Macromolecules Secreted by Stem Cells Different types of stem cells including MSCs and induced pluripotent stem cells (iPSCs) have been shown to differentiate to joint tissue cells such as osteoblasts, osteocytes, chondrocytes, tenocytes, fibroblasts, notochordal cells, and/or nucleus pulposus cells. While differentiating, the cells secret characteristic extracellular molecules such as aggrecan, glycosaminoglycans (GAGs), collagens and more.

A way to monitor the secretion of these molecules in a chip will include the use of micro MRI using different pulse sequences, including but not limited to: chemical exchange saturation transfer (CEST)-GAGs measurement; pH measurement Tl rho—GAGs measurement, magnetization transfer contrast (MTC)-collagen measurement, magnetization exchange (MEX)-collagen and osteoid measurement.

Chemical exchange saturation transfer (CEST) also provides the ability to analyze the GAG content in cartilage. The most common method for acquisition of a CEST data set is to acquire multiple image data sets with presaturation at different offset frequencies around the water resonance and one reference data set without saturation or with saturation at a very large offset frequency. The normalized signal as a function of the presaturation offset (termed the z-spectrum) can then be used to determine and quantify CEST effects, which are asymmetric with respect to the water resonance (i.e., a CEST effect appears either up- or downfield from water and therefore can be extracted from the z-spectrum via analysis of its asymmetry with respect to the water resonance). Chemical exchange saturation transfer (CEST) is a magnetic resonance imaging (MRI) contrast enhancement technique that enables indirect detection of metabolites with exchangeable protons. Endogenous metabolites with exchangeable protons including many endogenous proteins with amide protons, glycosaminoglycans (GAG), glycogen, myo-inositol (MI), glutamate (Glu), creatine (Cr) and several others have been identified as potential in vivo endogenous CEST agents. These endogenous CEST agents can be exploited as non-invasive and non-ionizing biomarkers of disease diagnosis and treatment monitoring.

Magnetization Transfer Contrast (MTC) MRI is an imaging method that evolved from NMR spectroscopy. In tissue imaging, MTC relies upon the interaction of less mobile protons associated with macromolecules such as proteins and their interactions with protons freely associated with water. The premise is that in a system where molecules move and exchange position, whether it be a change in spatial position in asymmetrical molecules or an exchangeable proton between a molecule and water, the magnetization state will also move and be transferred.

A two pool model can be utilized to illustrate the theory behind MTC MRI. Conventional MRI detects only the free water pool while the macromolecular pool remains mostly undetected. Both the macromolecular and free water pools are centered around the same frequency but the macromolecular pool is shallower and wider. Saturation is achieved by applying an off-resonance radio frequency (RF) pulse specific to a peak in the macromolecular pool before excitation at the center frequency. The RF pulse saturates the signal from the section leading to ideally no signal at the off-resonance frequency. Since both pools interact this saturation is transferred to the free water pool. While it is not possible to detect the changes in the macromolecular pool directly, it can be assumed that the loss in signal intensity of the free water pool corresponds to the changes in the macromolecular pool.

Ideally, an increase is preferable to a decrease in signal intensity since it is easier to visualize changes in brightness over changes in darkness. To achieve this type of image, a Magnetization Transfer Ratio (MTR) is calculated using a base image without saturation to measure the relative loss of signal intensity in a pixel by pixel basis: MTR=Nonsaturated-Saturated/Nonsaturated. MTC is very similar in function to CEST. CEST focuses on a limited part of magnetization transfer by linking it to chemical exchange systems.

Quantitative magnetization transfer (qMT) imaging is MR technique which utilizes a two-pool model of magnetization exchange to acquire information regarding the cartilage macromolecular matrix. qMT imaging techniques typically require multiple MT-contrast images with different magnetization preparatory pulses resulting in long scan times which have limited cartilage assessment to ex-vivo specimens. Cross-relaxation imaging (CRI) is a qMT method which can create three-dimensional parametric maps of articular cartilage measuring the fraction of macromolecular bound protons (f), the exchange rate constant between macromolecular bound protons and free water protons (k), and the T2 relaxation time of macromolecular bound protons (T2B) with high resolution and relatively short scan time based upon a limited number of MT-contrast images. The parameter f provides an indirect measure of macromolecular content, while the parameters k, and T2B reflect the efficiency of magnetization exchange between macromolecular bound protons and free water protons and the spin diffusion between proton sites in macromolecules respectively which may be influenced by macromolecular organization and ultra-structure Example 6

Micro Imaging for Non Invasive Monitoring of Osteogenic Cells-on-Chip

Microfluidic culture devices are attractive systems to model physiological and pathological conditions of tissues and organs. Although these devices allow fluorescent and light microcopy imaging of cultured cells, one of its current limitations is that various types of analyses require sacrificing of the culture. The Inventors have previously utilized micro imaging systems to monitor stem cell differentiation in ex-vivo 3D tissue constructs.

Of interest is utilizing optical imaging to non-invasively monitor stem cell survival and differentiation while cultured in an "organ-on-chip" device. Stiffer membrane and microfluidic environment will promote more efficient osteogenic differentiation.

To explore this possibility, the organ-on-chip was coated with ECM crosslinked with UV prior to cell seeding. Then mesenchymal stem cell line overexpressing BMP2 and Luciferase reporter genes were seeded on the coated organ-on-a-chip (see dimensions and the set up for microfluidic studies in FIG. 1 and supplemented with osteogenic media. The static cultures were performed using 200 μl media reservoirs that were changed every other day. The flow studies were performed using 30 μl/l flow of media pulled through using specialized pump (FIG. 1). Micrographs were taken twice a week and survival of the cells was monitored using bioluminescent imaging. The media was changed to media with Luciferin and imagined using IVIS (Perkin Elmer). The osteogenic differentiation after 3 weeks of culture in osteogenic media was monitored using florescent probes OsteoSense650 and BoneTag800 that were introduced 24 hours before the imaging and were imaged using fluorescent imaging (FLI) and near infrared (NIR) imaging, confocal microscopy and immunostaining.

Example 7

Monitoring Cell Proliferation without Harvest or Culture Disruption

A comparison of chips grown in static culture condition to chips grown under constant flow of media (30 μl/l) was performed along with evaluation of the effect of the flow on cell survival/proliferation of cells and the extent of osteogenic differentiation. The microscopic images (FIG. 1) show proliferation of the cells under the flow conditions, however it is difficult to quantify the extent of proliferation using this method without disrupting the cultures. Therefore, the Inventors used cell that express Luciferase reporter gene and the cell proliferation was quantified using bioluminescent imaging (BLI) twice a week (FIG. 2B, C). This imaging method allowed monitor the proliferation of the cells without the need to harvest or disrupt the culture and significant advantage to the flow system was observed. Also microfluidic environment had positive effect on osteogenic differentiation, when compared with static cultures.

Figures 3, 3C:
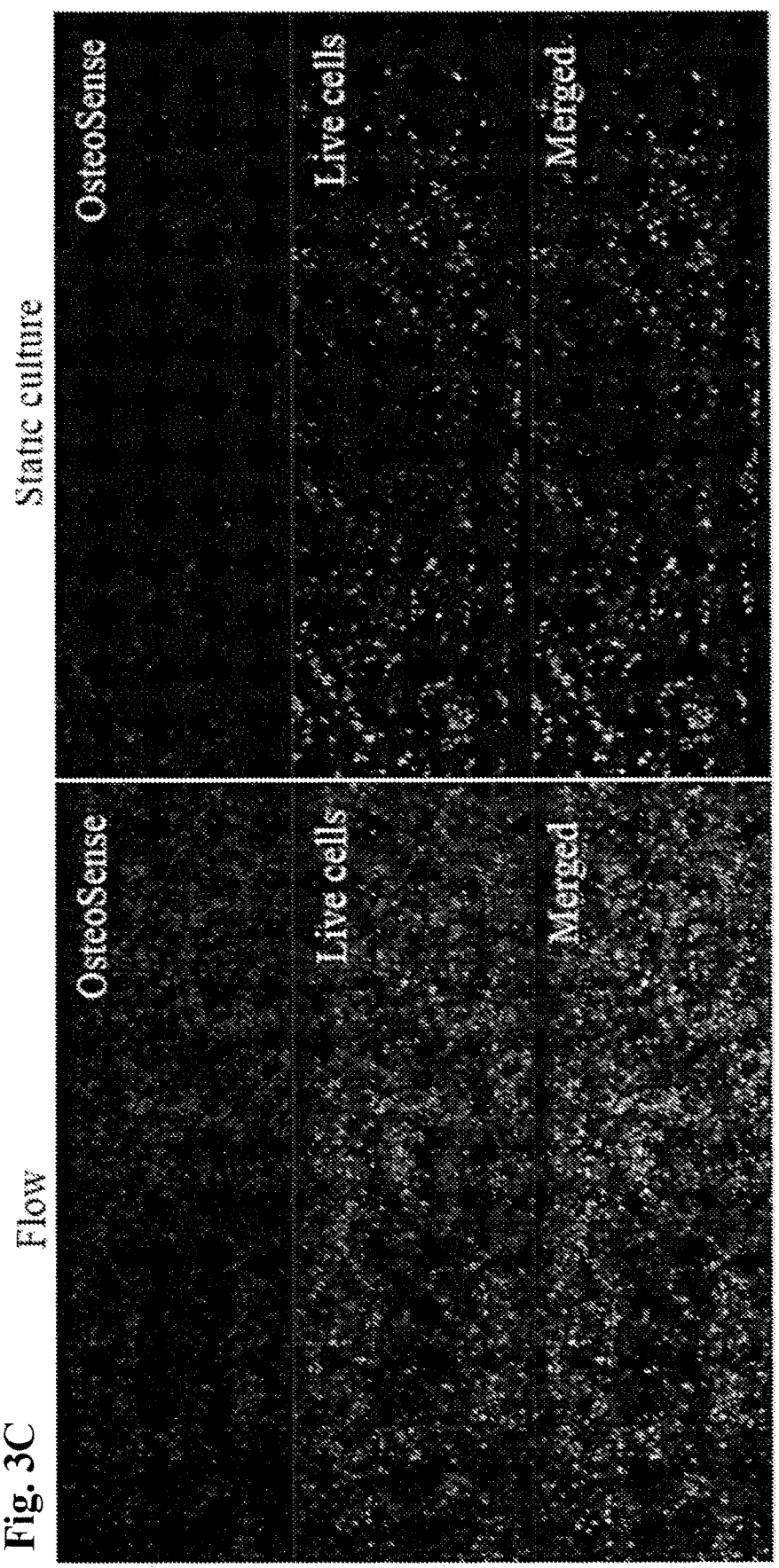
Figure 3D:
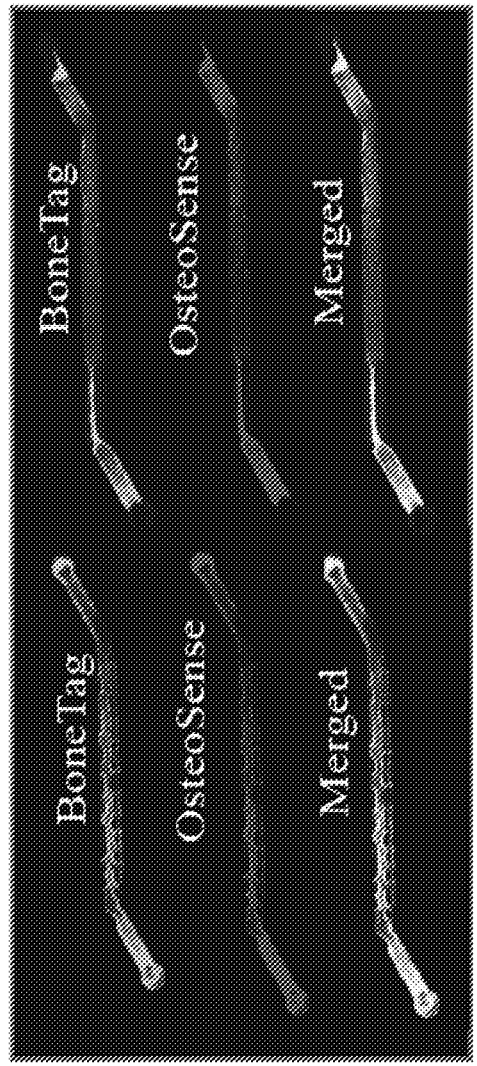
Figure 3D:
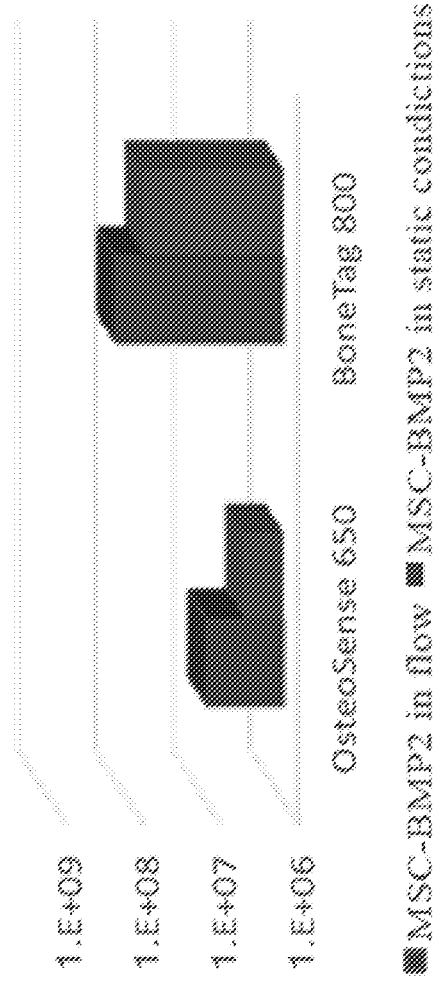

This effect was observed in fluorescent imaging of osteogenic differentiation probes using two different systems—FLI and Near Infrared (FIG. 3A-D). The probes can be detected using different wavelengths of fluorescence, therefore both probes can be added simultaneously and imaged separately. The quantification of FLI (FIG. 3A, B) of BoneTag showed higher osteogenic differentiation of the cell under the flow conditions. OsteoSense was also imaged using confocal microscopy in conjugation with Live/Dead staining (FIG. 3C) showing that most of the live cells absorbed OsteoSense probe and again the flow chips were stained in more efficiently than the static cultures. The NIR system is considered more sensitive and the quantification of the image more accurate. Here, the Inventors demonstrate that they system is capable of detecting the same trend using both probes (FIG. 3D).

Example 8

Confirmation of Osteogenic Differentiation

Figure 4:
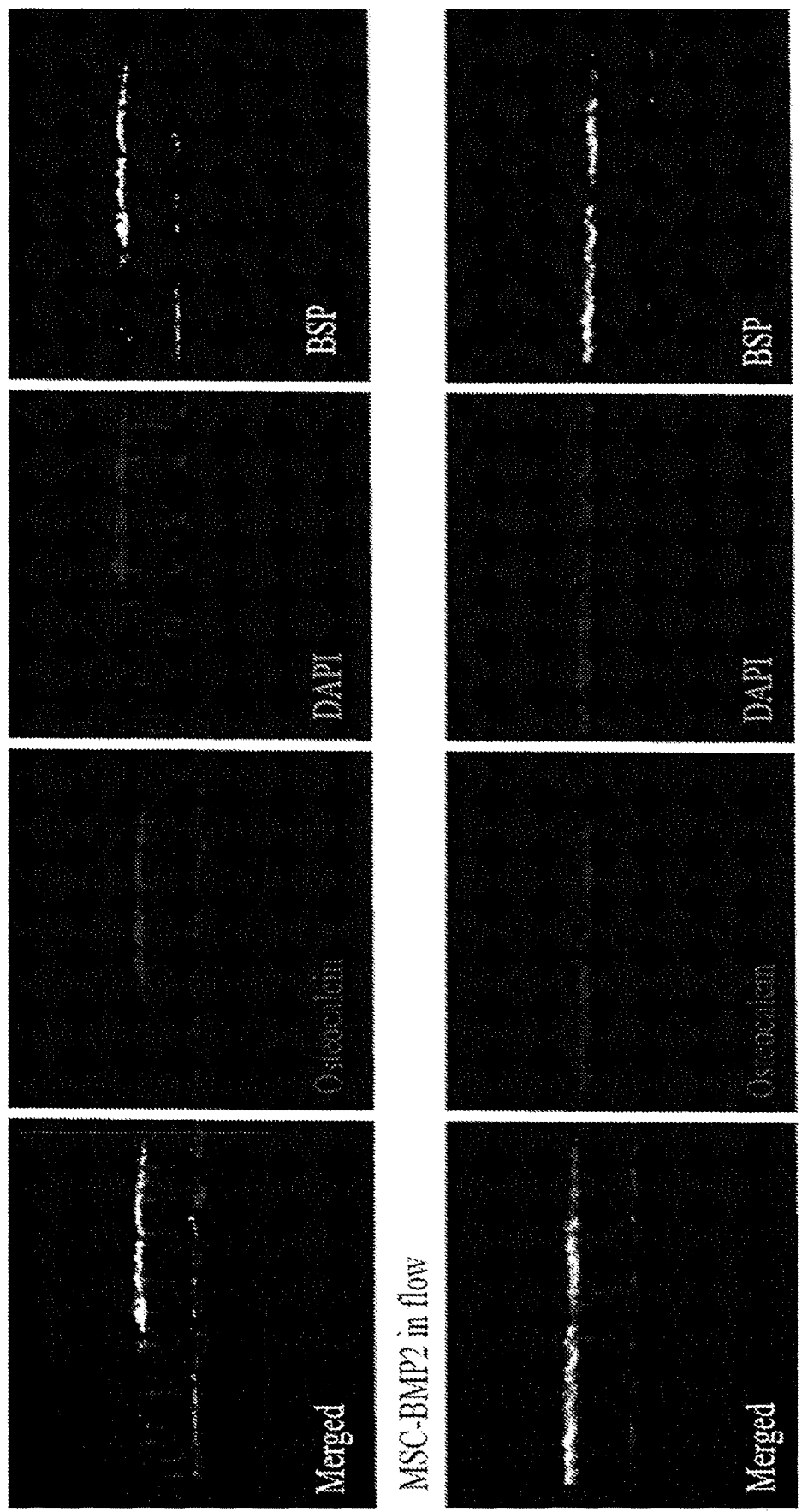
FIG. 4. Immunostaining of osteogenic differentiation of MSC-BMP2 in Organ-on-chip. The chips were sectioned using vibratome across the channels. The sections were stained using with immunofluorescent staining against the osteogenic markers osteocalcin and bone sialoprotein (BSP), and imaged using confocal microscopy.
Figure 5A:
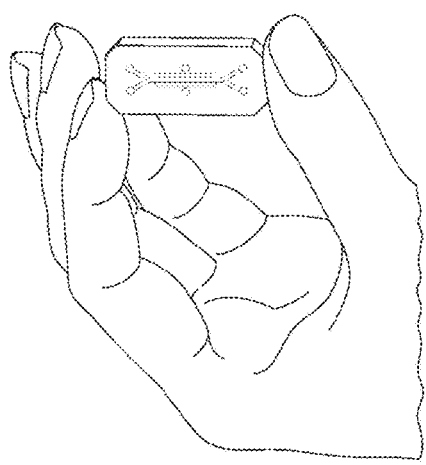
FIG. 5A-B. Image of Bone-Chip and diagram illustrating the workings of Chip. The PDMS Chip (FIG. 5A) contains a middle channel with a porous flexible membrane upon which the cells are seeded after coating with appropriate extracellular matrix (FIG. 5B).
Figure 5B:
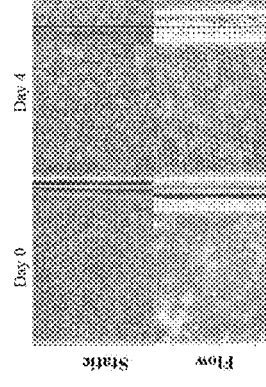

In order to confirm osteogenic differentiation of the MSSC-BMP2 cells, the harvested chips were sectioned using vibratome creating transvers sections across the channels. Then these sections were subjected to immunofluorescent staining using primary antibody against Osteocalcin and Bone Sialoprotein (BSP) osteogenic markers. The staining shows cells on both sides of the membrane in both conditions, but mainly in the top channel. In both conditions there was positive staining for both marker, indicating osteogenic differentiation, however the staining looks more prominent in the chips that were cultured in flow (FIG. 4 bottom panel).

Example 9

Methods

Generation of MSC-Tet-Off-BMP2 Cell with Constitutive Luc Reporter Gene Expression Generation of rhBMP-2 overexpressing MSCs was described previously[23]. Briefly, cells from the C3H10T1/2 MSC line were stably transfected with a ptTATop-BMP2 plasmid vector that encodes for a tetracycline transactivator and rhBMP-2 (creating a tet-off system). Using the inducible human BMP-2 expression vector, ptTATop-BMP2, the expression of hBMP-2 could be shut down by administration of doxycycline, an analogue of tetracycline, or turned on by doxycycline absence. Then, the cells were transfected with a Lenti-viral vector encoding for Luc2 reporter gene under the constitutively expressed ubiquitin promotor[22]. Cells were cultured in 100-mm culture plates in a complete growth medium (Dulbecco's modified Eagle's medium containing 10% fetal bovine serum, 2 mM L-glutamine, 100 U/mL penicillin, and 100 U/mL streptomycin (Gibco-Life Technologies, Carlsbad, CA) in a 5% $CO_2$/95% air atmosphere at 37° C. 1 mg/mL Doxycycline was added to the medium to prevent cell differentiation before seeding onto the chips.

Bone-Chip System

Soft lithography was used to prepare the chips with polydimethylsiloxane (PDMS). The chips were then covalently coated with 50 ug/mL Laminin in PBS (Sigma), using ER1/2 cross-linker (Emulate, Inc.) and exposure to UV light [356 mm, 20 min]. Before the chip studies commenced, the cells were trypsinized and centrifuged at 300 g and 4° C. for 5 min. The cells were counted using the Trypan blue exclusion test and seeded on the coated chips in $1\times10^6$ cells/ml concentration in high glucose complete growth media supplemented with 1 μg/ml Doxycycline to prevent BMP2 expression. 50 μl of cell suspension was applied into the top channel. Dead/non-adhered cells were removed after 3-6 hours by flushing media through the device and flow was started 24 hrs after seeding at a rate 30 μl/hr of media pulled through, using a specialized pump. The static cultures were performed using 200 μl media reservoirs that were changed every other day. Once the cells reached confluence (2-3 days), the growth media was replaced by Doxycycline-deficient osteogenic media (10 mM β-glycerophosphate, 50 g L-Ascorbic acid).

Cell Growth and Viability

Micrographs were taken twice a week for two weeks using EVOS light microscopy (ThermoFisher, Waltham, MA). Cell survival was monitored biweekly using Bioluminescent Imaging (BLI); the media was changed to media supplemented with [0.126 μg/μl] Luciferin, and the BLI signal was captured immediately using Xenogen IVIS Spectrum (PerkinElmer, Waltham, MA), 1 min exposure time. The image analysis was done using total influx data calculated on the same size ROI, normalized to background noise in each image.

Non-Invasive Osteogenic Differentiation Assessment (FLI, NIR—OsteoSense[650]/BoneTag)

The osteogenic differentiation was evaluated after 3 weeks of culture in osteogenic media using florescent probes. Data herein compared tetracycline-deprived in static and flow culture, and used non-differentiating cells supplemented with tetracycline as a negative control. OsteoSense[650] (Perkin Elmar) 0.625 nmol and BoneTag[800] (LI-COR Biosciences, Lincoln, NE) 2.56 nmol were introduced 24 hours before the imaging, and were imaged using fluorescent imaging (FLI) and near infrared imaging (NIRI) systems—using IVIS Xenogen for the former, Odyssey® CLx Imaging System (LI-COR Biosciences) for the later.

Gene Expression Analysis

Total RNA was isolated using RNAeasy isolation kit (Qiagen, Hilden, Germany) on week 3 of osteogenic differentiation. Single-stranded cDNA was created with the aid of a reverse transcription kit (Invitrogen) and employed as a template for real time-PCR with Taqman® gene expression assays using ABI7500 Prism (Applied Biosystems, Carlsbad, CA), as previously described[36]. Quantitative RT-PCR was performed to quantify the expression of the osteogenic genes Osteopontin (Opn), Collagen 1 (Col1) and Bonesialoprotein (BSP). The house keeping gene 18S was used as a to normalize the data, non-differentiating cells (Day 0) were used as calibrator sample to quantify the relative gene expression (RQs).

Immunofluorescence

Four weeks after seeding, the cells were fixed for immunostaining using 4% formaldehyde. Nonspecific antigens were blocked by applying blocking serum-free solution (Dako, Santa Clara, CA). Chips were stained with primary antibodies against mouse BSP (1:100 Cat #MBS176061, MyBiosourse, San Diego, CA), Col1 (1:250 Cat #ab21286, Abcam, Cambridge, MA) and OC (1:100 Cat #PA1-85754, ThermoFisher Scientific) to examine osteogenic differentiation. The primary antibodies were applied into the chips, incubated in 4° C. overnight, and washed off using PBS; the chips were then incubated with secondary antibodies (Supplemental Table 1) for 1 hr in room temperature, after which they were washed off with PBS. The chips were then stained with 4',6-diamidino-2-phenylindole dihydrochloride (DAPI, 1 g/ml) for 5 min in the dark, after which they were again washed 3 times with PBS. A VectaMount mounting medium (Vector Laboratories, Burlingame, CA) was applied into the Bone-Chip. The chips were imaged using a 4-channel Laser Scanning Microscope 780 (Zeiss, Pleasanton, CA) with 10× magnification, z-stacking, and tile scanning. For zoom-in images, a single z-stacked image was generated using 10× magnification. All chips were scanned using the same gain and exposure settings.

Example 10

Viability

The cell proliferation of cells that were grown on the Bone-Chips that were under constant flow of media (30 μl/h) was elevated comparing to the cells grown in static conditions. The microscopic images show proliferation of the cells under both static and flow conditions, achieving 100% confluence 14 days after seeding (FIG. 6A). However, the BLI signal generated by the constitutively expressed Luciferase reporter gene, reflecting the cell survival and proliferation, demonstrated notable advantage to the flow system in qualitative analysis (FIG. 6B). Quantitative analysis showed significantly higher signal in the flow-culture group beginning a week after cell seeding (FIG. 6C). The cells in the flow chips demonstrated elevation in the measured BLI signal indicating proliferation, while the cells in the static group has yielded a constant BLI signal indicating survival, but no proliferation.

Example 11

Optical Imaging of Osteogenesis

Figure 7A:
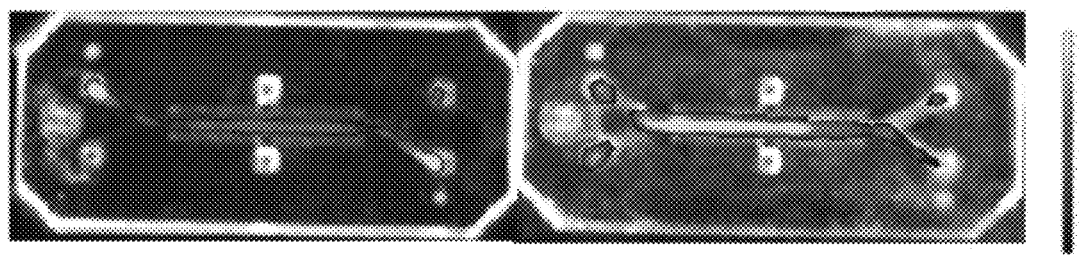
FIG. 7A-F. Live-monitoring of MSCs osteogenic differentiation on a Bone-Chip. The differentiation was evaluated three weeks after seeding with OsteoSense650 and BoneTag800 probes, that were added to the media for 24 h and washed off prior to imaging performed using two different imaging systems; fluorescent imaging system (FIG. 7A), the labeling was quantified using IVIS (B&C for OsteoSense$^{650}$ and BoneTag$^{800}$, respectively. n=5, $*p<0.05$; $***P<0.001$ Bars indicate standard deviation), and Near Infrared imaging system (FIG. 7D, NIRI performed using Odyssey® CLx, Li-Cor), which allowed quantification as well (n=5, $*p<0.05$; $***P<0.001$ Bars indicate standard deviation).
Figure 7B:
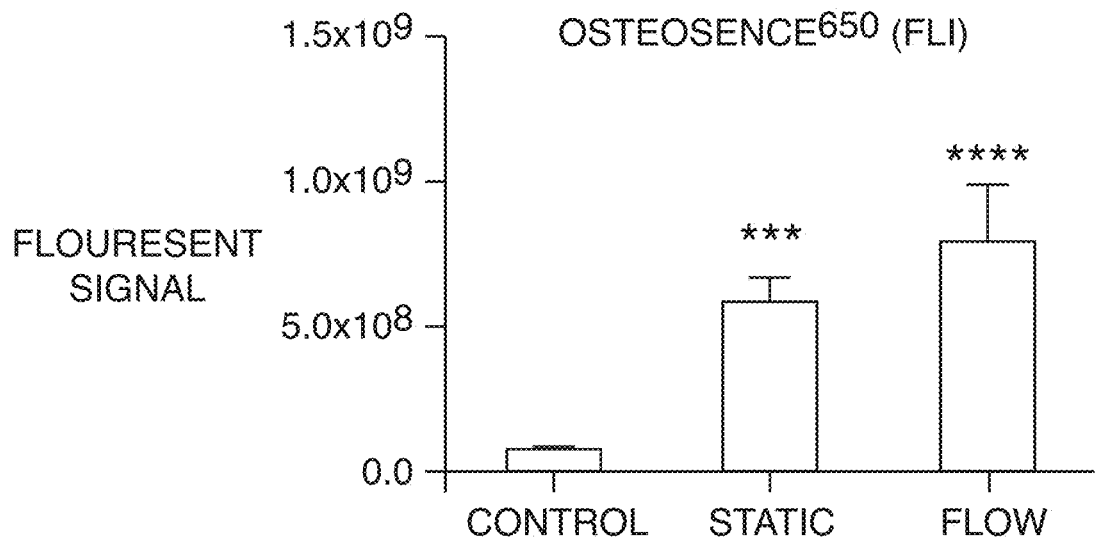
Figure 7C:
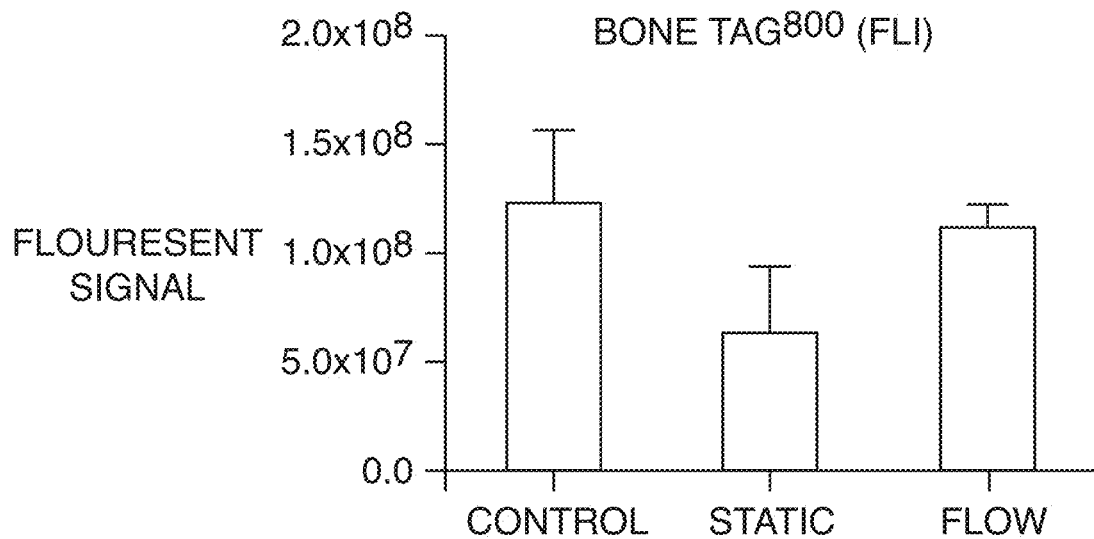
Figure 7D:
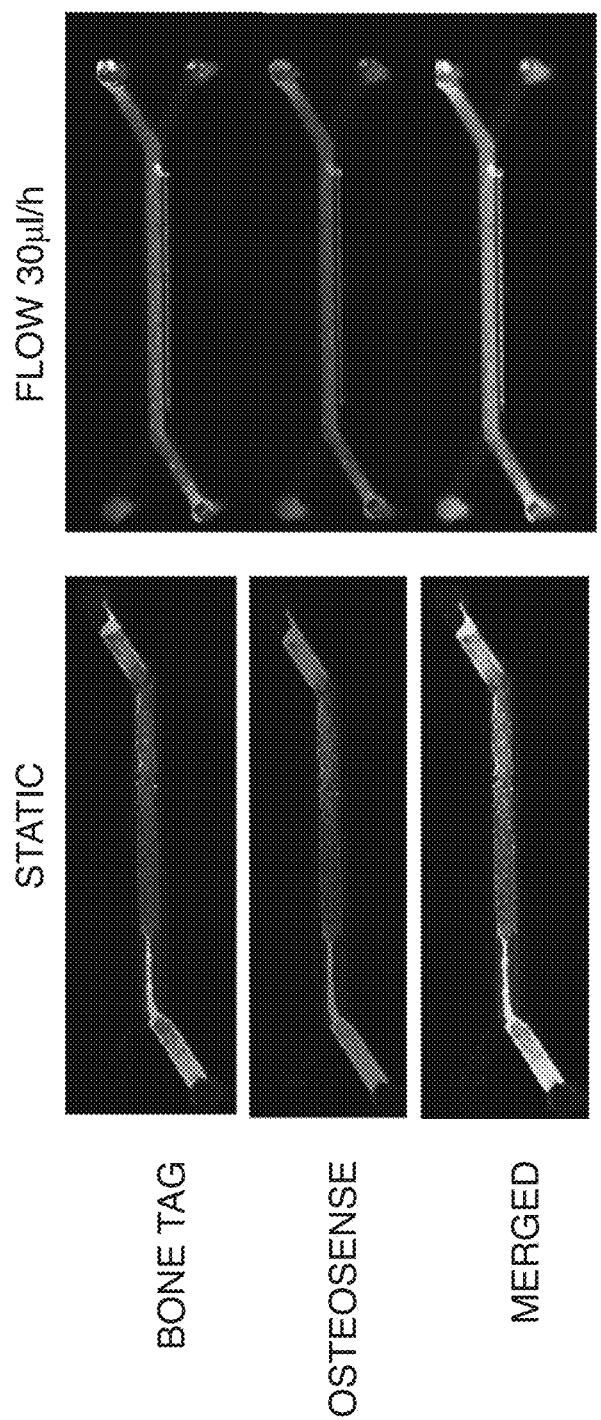
Figure 7E:
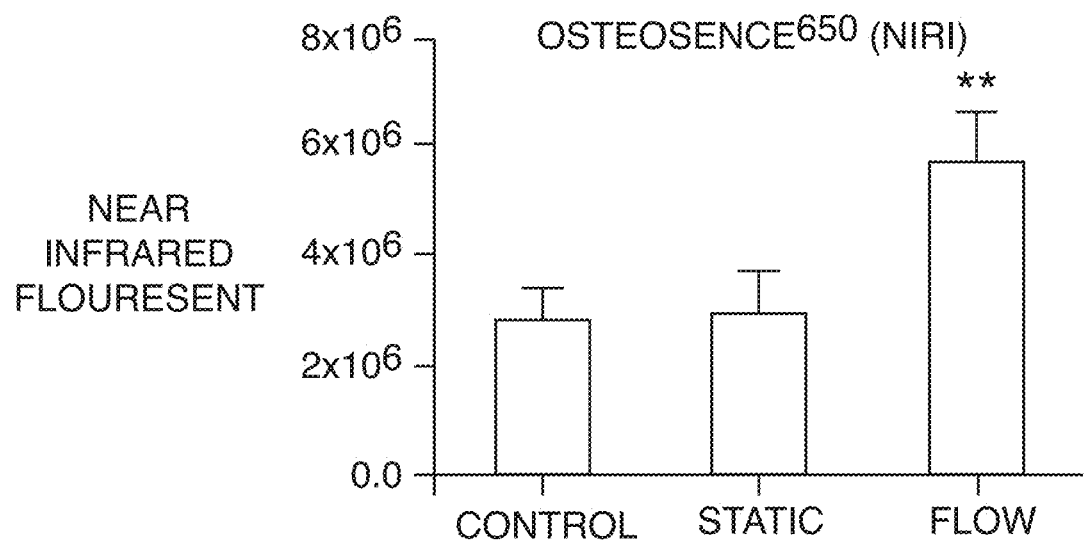
Figure 7F:
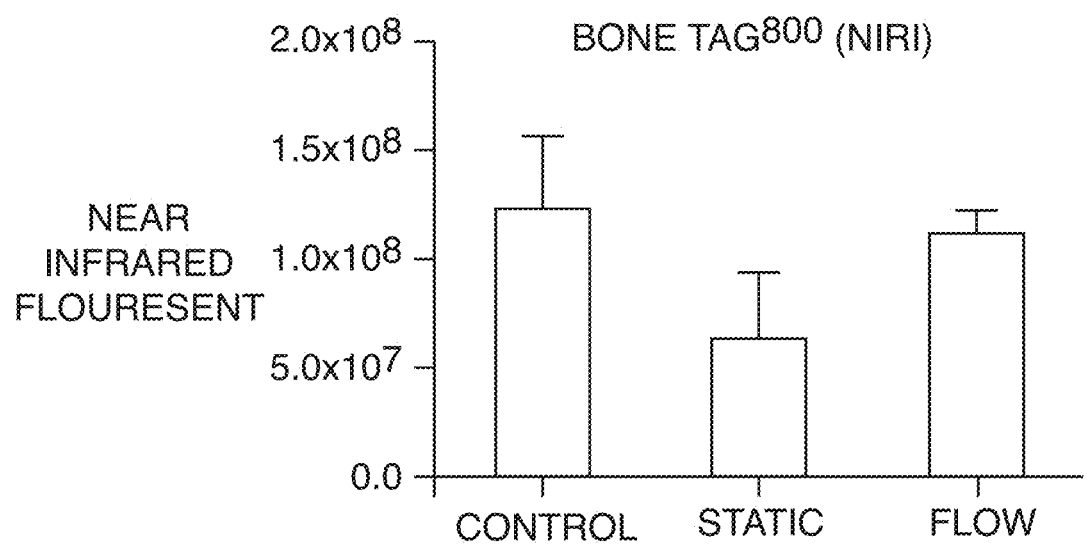

The micro-engineered environment with flow had positive effect on osteogenic differentiation, when compared with static cultures (FIG. 7A-F-8A-E). This effect was observed in fluorescent imaging of osteogenic differentiation probes using two different systems—FLI and NIRI (FIG. 7A-F). The probes can be detected using different wavelengths of fluorescence, therefore both probes could be added simultaneously and imaged separately. The quantification of FLI of OsteoSense[650], performed three weeks after seeding, showed significantly higher osteogenic differentiation of the cells under the flow conditions, and both were significantly higher than the control, MSC-BMP2 cells in which differentiation was halted by tetracycline supplementation (FIG. 7A,B). The fluorescent signal measured in the static and the flow cultures was higher than the control, the static by significance of $P<0.05$ while the flow by significance of $P<0.001$. However, most of the live cells given BoneTag[800] probes produced a very low BoneTag[800] FLI signal, comparable to the control cells (FIG. 7C). The NIRI system is considered more sensitive and provides a more accurate quantification of signal. Data herein show that this system is capable of detecting a similar trend (FIG. 7D); the OsteoSense[650] signal detected by NIRI was significantly higher in the flow culture comparing to both static culture and control (FIG. 7E), while the use of BoneTag[800] probe did not produced signal higher than the control using both imaging systems (FIG. 7F).

Example 12

Gene Expression

Figure 8:
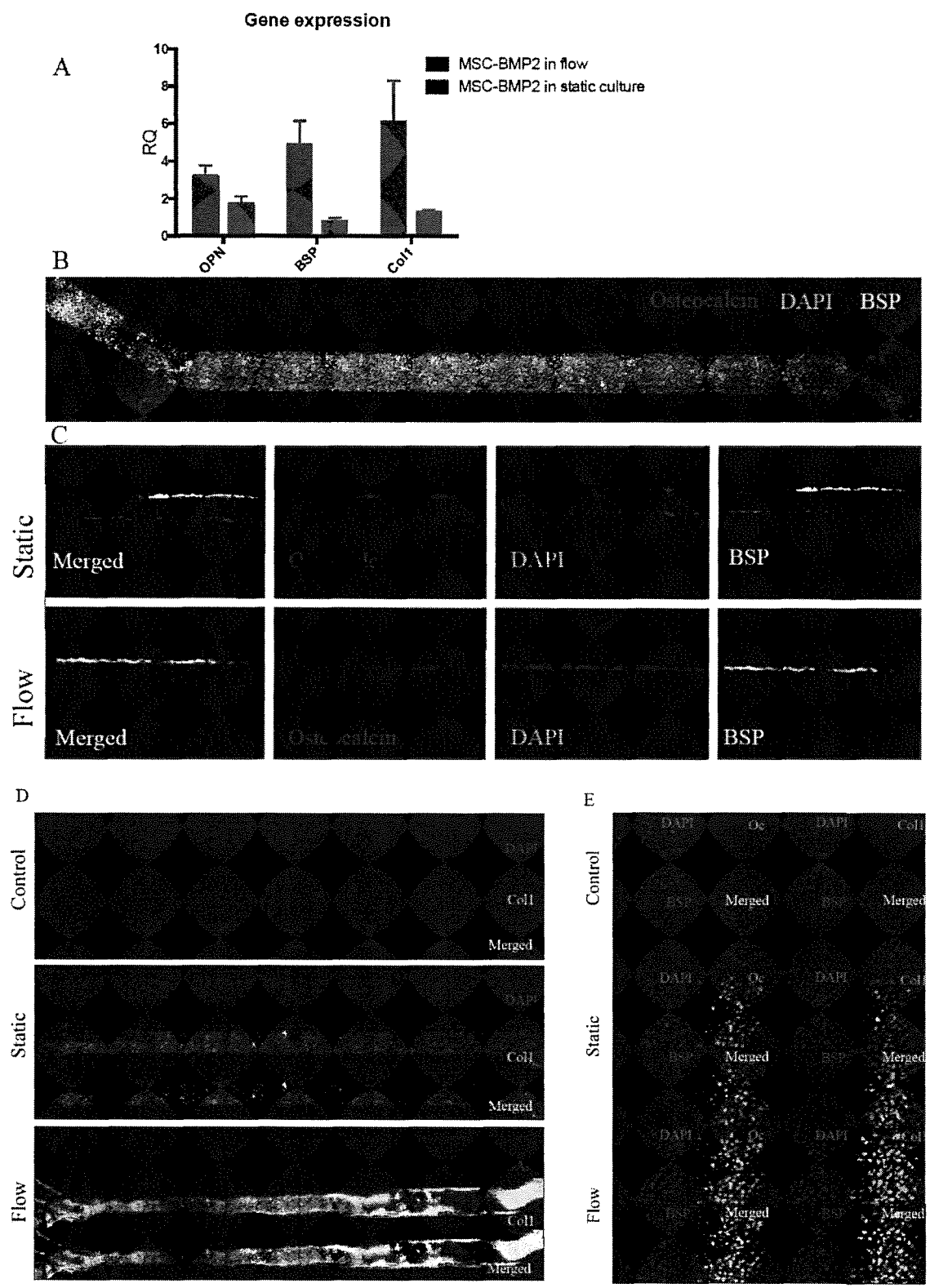
FIG. 8A-E. Validation of MSC-BMP2 differentiation in a Bone Chip. Gene expression of the osteogenic markers Osteopontin (OPN), Bone-sialoprotin (BSP) and Collagen-1 (Col1) was evaluated 3 weeks after seeding using qRT-PCR (FIG. 8A, n=5, $*p<0.05$; Bars indicate standard deviation). The cells were fixed and fluorescently stained against the osteogenic markers Osteocalcin and BSP in the whole chips, and imaged in 10× magnification (FIG. 8B). Other Bone-Chips were sectioned using vibratome across the channels, stained for the same markers (FIG. 8C). Whole chips were stained for Col1 and the entire chip was imaged using confocal microscopy (FIG. 8D). In other sample set staining was performed against Osteocalcin (Oc), BSP and Col1 (FIG. 8E).

The gene expression analysis, performed after three weeks of culture in osteogenic media to validate the findings obtained by imaging methods. The analysis confirmed the osteogenic differentiation of the MSC-BMP2 cells in both static and flow conditions, showing overexpression of Osteopontin (OPN), Collagen type 1 and Bone Sialoprotein (BSP) in all cells, but significantly higher expression of all the genes was observed in the cells cultured in flow conditions comparing to static culture (FIG. 8A). All three examined genes were elevated in the static culture to 1-2 times comparing to non-differentiating cells, while in the flow cultured cells the OPN expression was tripled, the BSP expression raised by factor 5 and the Collagen-1 expression was increased by factor 6.

Example 13

Immunofluorescence

To further affirm the imaging results, immunofluorescent staining was performed against the Osteocalcin and BSP markers on whole Bone-Chips (FIG. 8B) and transverse sections across the channels (FIG. 8C). The staining shows cells on both sides of the membrane in both conditions, but mainly in the top channel. In both conditions, there was positive staining for both marker, indicating osteogenic differentiation, however the staining is more prominent in the Bone-Chips that were cultured under flow. After staining against Collagen-1 in the whole chip, confocal microscopy revealed prominent expression in the flow group, while only mild expression was detected in the static cultured chip, comparing to null expression in the control group (FIG. 8D).

REFERENCES

1. Gomes, M. E., Rodrigues, M. T., Domingues, R. M. A. & Reis, R. L. Tissue Engineering and Regenerative Medicine: New Trends and Directions-A Year in Review. Tissue Eng Part B Rev 23, 211, 2017.
2. Bhatia, S. N. & Ingber, D. E. Microfluidic organs-on-chips. Nat Biotechnol 32, 760, 2014.
3. Sung, J. H., Esch, M. B., Prot, J. M., Long, C. J., Smith, A., Hickman, J. J. & Shuler, M. L. Microfabricated mammalian organ systems and their integration into models of whole animals and humans. Lab Chip 13, 1201, 2013.
4. Maschmeyer, I., Lorenz, A. K., Schimek, K., Hasenberg, T., Ramme, A. P., Hübner, J., Lindner, M., Drewell, C., Bauer, S., Thomas, A., Sambo, N. S., Sonntag, F., Lauster, R. & Marx, U. A four-organ-chip for interconnected long-term co-culture of human intestine, liver, skin and kidney equivalents. Lab Chip 15, 2688, 2015.
5. Esch, E. W., Bahinski, A. & Huh, D. Organs-on-chips at the frontiers of drug discovery. Nat Rev Drug Discov 14, 248, 2015.
6. Bhise, N. S., Ribas, J., Manoharan, V., Zhang, Y. S., Polini, A., Massa, S., Dokmeci, M. R. & Khademhosseini, A. Organ-on-a-chip platforms for studying drug delivery systems. J Control Release 190, 82, 2014.
7. Zhang, Y. S., Zhang, Y. N. & Zhang, W. Cancer-on-a-chip systems at the frontier of nanomedicine. Drug Discov Today 2017.
8. Shuler, M. L. Organ-, body- and disease-on-a-chip systems. Lab Chip 17, 2345, 2017.
9. Huh, D., Hamilton, G. A. & Ingber, D. E. From 3D cell culture to organs-on-chips. Trends Cell Biol 21, 745, 2011.
10. Zhang, Y. S., Arneri, A., Bersini, S., Shin, S. R., Zhu, K., Goli-Malekabadi, Z., Aleman, J., Colosi, C., Busignani, F., Dell'Erba, V., Bishop, C., Shupe, T., Demarchi, D., Moretti, M., Rasponi, M., Dokmeci, M. R., Atala, A. & Khademhosseini, A. Bioprinting 3D microfibrous scaffolds for engineering endothelialized myocardium and heart-on-a-chip. Biomaterials 110, 45, 2016.
11. Kim, S., Lee, H., Chung, M. & Jeon, N. L. Engineering of functional, perfusable 3D microvascular networks on a chip. Lab Chip 13, 1489, 2013.
12. Homan, K. A., Kolesky, D. B., Skylar-Scott, M. A., Herrmann, J., Obuobi, H., Moisan, A. & Lewis, J. A. Bioprinting of 3D Convoluted Renal Proximal Tubules on Perfusable Chips. Sci Rep 6, 34845, 2016.
13. Kim, H. J., Huh, D., Hamilton, G. & Ingber, D. E. Human gut-on-a-chip inhabited by microbial flora that experiences intestinal peristalsis-like motions and flow. Lab Chip 12, 2165, 2012.
14. Bhise, N. S., Manoharan, V., Massa, S., Tamayol, A., Ghaderi, M., Miscuglio, M., Lang, Q., Shrike Zhang, Y., Shin, S. R., Calzone, G., Annabi, N., Shupe, T. D., Bishop, C. E., Atala, A., Dokmeci, M. R. & Khademhosseini, A.

A liver-on-a-chip platform with bioprinted hepatic spheroids. Biofabrication 8, 014101, 2016.
15. Wobma, H. & Vunjak-Novakovic, G. Tissue Engineering and Regenerative Medicine 2015: A Year in Review. Tissue Eng Part B Rev 22, 101, 2016.
16. Kolesky, D. B., Homan, K. A., Skylar-Scott, M. A. & Lewis, J. A. Three-dimensional bioprinting of thick vascularized tissues. Proc Natl Acad Sci USA 113, 3179, 2016.
17. Benayahu, D., Kletter, Y., Zipori, D. & Wientroub, S. Bone marrow-derived stromal cell line expressing osteoblastic phenotype in vitro and osteogenic capacity in vivo. J Cell Physiol 140, 1, 1989.
18. Syftestad, G. T., Weitzhandler, M. & Caplan, A. I. Isolation and characterization of osteogenic cells derived from first bone of the embryonic tibia. Dev Biol 110, 275, 1985.
19. Hoemann, C. D., El-Gabalawy, H. & McKee, M. D. In vitro osteogenesis assays: influence of the primary cell source on alkaline phosphatase activity and mineralization. Pathol Biol (Paris) 57, 318, 2009.
20. Ben Arav, A., Pelled, G., Zilberman, Y., Kimelman-Bleich, N., Gazit, Z., Schwarz, E. M. & Gazit, D. Adeno-associated virus-coated allografts: a novel approach for cranioplasty. J Tissue Eng Regen Med 6, e43, 2012.
21. Cohn Yakubovich, D., Tawackoli, W., Sheyn, D., Kallai, I., Da, X., Pelled, G., Gazit, D. & Gazit, Z. Computed Tomography and Optical Imaging of Osteogenesis-angiogenesis Coupling to Assess Integration of Cranial Bone Autografts and Allografts. J Vis Exp 2015.
22. Sheyn, D., Kallai, I., Tawackoli, W., Cohn Yakubovich, D., Oh, A., Su, S., Da, X., Lavi, A., Kimelman-Bleich, N., Zilberman, Y., Li, N., Bae, H., Gazit, Z., Pelled, G. & Gazit, D. Gene-modified adult stem cells regenerate vertebral bone defect in a rat model. Mol Pharm 8, 1592, 2011.
23. Moutsatsos, I. K., Turgeman, G., Zhou, S., Kurkalli, B. G., Pelled, G., Tzur, L., Kelley, P., Stumm, N., Mi, S., Muller, R., Zilberman, Y. & Gazit, D. Exogenously regulated stem cell-mediated gene therapy for bone regeneration. Mol Ther 3, 449, 2001.
24. Pelled, G., Tai, K., Sheyn, D., Zilberman, Y., Kumbar, S., Nair, L. S., Laurencin, C. T., Gazit, D. & Ortiz, C. Structural and nanoindentation studies of stem cell-based tissue-engineered bone. J Biomech 40, 399, 2007.
25. Tai, K., Pelled, G., Sheyn, D., Bershteyn, A., Han, L., Kallai, I., Zilberman, Y., Ortiz, C. & Gazit, D. Nanobiomechanics of repair bone regenerated by genetically modified mesenchymal stem cells. Tissue Eng Part A 14, 1709, 2008.
26. Aslan, H., Zilberman, Y., Arbeli, V., Sheyn, D., Matan, Y., Liebergall, M., Li, J. Z., Helm, G. A., Gazit, D. & Gazit, Z. Nucleofection-based ex vivo nonviral gene delivery to human stem cells as a platform for tissue regeneration. Tissue Eng 12, 877, 2006.
27. Ryoo, H. M., Lee, M. H. & Kim, Y. J. Critical molecular switches involved in BMP-2-induced osteogenic differentiation of mesenchymal cells. Gene 366, 51, 2006.
28. Hasharoni, A., Zilberman, Y., Turgeman, G., Helm, G. A., Liebergall, M. & Gazit, D. Murine spinal fusion induced by engineered mesenchymal stem cells that conditionally express bone morphogenetic protein-2. J Neurosurg Spine 3, 47, 2005.
29. Xie, C., Reynolds, D., Awad, H., Rubery, P. T., Pelled, G., Gazit, D., Guldberg, R. E., Schwarz, E. M., O'Keefe, R. J. & Zhang, X. Structural bone allograft combined with genetically engineered mesenchymal stem cells as a novel platform for bone tissue engineering. Tissue Eng 13, 435, 2007.
30. Kimelman-Bleich, N., Pelled, G., Sheyn, D., Kallai, I., Zilberman, Y., Mizrahi, O., Tal, Y., Tawackoli, W., Gazit, Z. & Gazit, D. The use of a synthetic oxygen carrier-enriched hydrogel to enhance mesenchymal stem cell-based bone formation in vivo. Biomaterials 30, 4639, 2009.
31. Huh, D., Matthews, B. D., Mammoto, A., Montoya-Zavala, M., Hsin, H. Y. & Ingber, D. E. Reconstituting organ-level lung functions on a chip. Science 328, 1662, 2010.
32. Korin, N., Kanapathipillai, M., Matthews, B. D., Crescente, M., Brill, A., Mammoto, T., Ghosh, K., Jurek, S., Bencherif, S. A., Bhatta, D., Coskun, A. U., Feldman, C. L., Wagner, D. D. & Ingber, D. E. Shear-activated nanotherapeutics for drug targeting to obstructed blood vessels. Science 337, 738, 2012.
33. Polacheck, W. J., German, A. E., Mammoto, A., Ingber, D. E. & Kamm, R. D. Mechanotransduction of fluid stresses governs 3D cell migration. Proc Natl Acad Sci USA 111, 2447, 2014.
34. Jain, A., van der Meer, A. D., Papa, A. L., Barrile, R., Lai, A., Schlechter, B. L., Otieno, M. A., Louden, C. S., Hamilton, G. A., Michelson, A. D., Frelinger, A. L. & Ingber, D. E. Assessment of whole blood thrombosis in a microfluidic device lined by fixed human endothelium. Biomed Microdevices 18, 73, 2016.
35. Zhang, Y., Gazit, Z., Pelled, G., Gazit, D. & Vunjak-Novakovic, G. Patterning osteogenesis by inducible gene expression in microfluidic culture systems. Integr Biol (Camb) 3, 39, 2011.
36. Zhang, X., Schwarz, E. M., Young, D. A., Puzas, J. E., Rosier, R. N. & O'Keefe, R. J. Cyclooxygenase-2 regulates mesenchymal cell differentiation into the osteoblast lineage and is critically involved in bone repair. J Clin Invest 109, 1405, 2002.
37. Sheyn, D., Yakubovich, D. C., Kallai, I., Su, S., Da, X., Pelled, G., Tawackoli, W., Cook-Weins, G., Schwarz, E. M., Gazit, D. & Gazit, Z. PTH Promotes Allograft Integration in a Calvarial Bone Defect. Mol Pharm 10, 4462, 2013.
38. Xu, H., Othman, S. F., Hong, L., Peptan, I. A. & Magin, R. L. Magnetic resonance microscopy for monitoring osteogenesis in tissue-engineered construct in vitro. Phys Med Biol 51, 719, 2006.
39. Tobias, G., Uwe, H. & Tobias, G. Pantoprazol inhibits the stimulating effect for bone formation of diclofenac in vitro evaluated by the novel method of 99m-Tc-HDP-Labeling in vitro. Journal of Nuclear Medicine 57, 2016.
40. Woolf, E. C., Curley, K. L., Liu, Q., Turner, G. H., Charlton, J. A., Preul, M. C. & Scheck, A. C. The Ketogenic Diet Alters the Hypoxic Response and Affects Expression of Proteins Associated with Angiogenesis, Invasive Potential and Vascular Permeability in a Mouse Glioma Model. PLoS One 10, e0130357, 2015.
41. Ocak, M., Gillman, A. G., Bresee, J., Zhang, L., Vlad, A. M., Müller, C., Schibli, R., Edwards, W. B., Anderson, C. J. & Gach, H. M. Folate receptor-targeted multimodality imaging of ovarian cancer in a novel syngeneic mouse model. Mol Pharm 12, 542, 2015.
42. Shanmugam, V. K., Tassi, E., Schmidt, M. O., McNish, S., Baker, S., Attinger, C., Wang, H., Shara, N. & Wellstein, A. Utility of a human-mouse xenograft model and in vivo near-infrared fluorescent imaging for studying wound healing. Int Wound J 12, 699, 2015.

43. Bergmann, S., Rohde, M., Schughart, K. & Lengeling, A. The bioluminescent *Listeria monocytogenes* strain Xen32 is defective in flagella expression and highly attenuated in orally infected BALB/cJ mice. Gut Pathog 5, 19, 2013.
44. Chang, J., Liu, F., Lee, M., Wu, B., Ting, K., Zara, J. N., Soo, C., Al Hezaimi, K., Zou, W., Chen, X., Mooney, D. J. & Wang, C. Y. NF-xB inhibits osteogenic differentiation of mesenchymal stem cells by promoting β-catenin degradation. Proc Natl Acad Sci USA 110, 9469, 2013.
45. Cohn Yakubovich, D., Sheyn, D., Bez, M., Schary, Y., Yalon, E., Sirhan, A., Amira, M., Yaya, A., De Mel, S., Da, X., Ben-David, S., Tawackoli, W., Ley, E. J., Gazit, D., Gazit, Z. & Pelled, G. Systemic administration of mesenchymal stem cells combined with parathyroid hormone therapy synergistically regenerates multiple rib fractures. Stem Cell Res Ther 8, 51, 2017.
46. Cohn Yakubovich, D., Eliav, U., Yalon, E., Schary, Y., Sheyn, D., Cook-Wiens, G., Sun, S., McKenna, C. E., Lev, S., Binshtok, A. M., Pelled, G., Navon, G., Gazit, D. & Gazit, Z. Teriparatide attenuates scarring around murine cranial bone allograft via modulation of angiogenesis. Bone 97, 192, 2017.
47. Wang, B., Lee, W. Y., Huang, B., Zhang, J. F., Wu, T., Jiang, X., Wang, C. C. & Li, G. Secretome of Human Fetal Mesenchymal Stem Cell Ameliorates Replicative Senescen. Stem Cells Dev 25, 1755, 2016.
48. Takebe, T., Zhang, B. & Radisic, M. Synergistic Engineering: Organoids Meet Organs-on-a-Chip. Cell Stem Cell 21, 297, 2017.

We claim:

1. A method of osteogenic differentiation comprising
a) seeding mesenchymal stem cells (MSCs) in a microfluidic device in growth medium containing doxycycline (DOX) in the absence of flow to produce attached MSCs,
b) flowing the growth medium in the absence of Bone Morphogenetic Protein-2 (BMP2) such that the attached MSCs proliferate to produce proliferated MSCs,
c) contacting the proliferated MSCs with an osteogenic medium containing Bone Morphogenetic Protein-2 (BMP2) to produce differentiated cells that express one or more of osteocalcin, bone sialoprotein (bsp), osteopontin (opn), and collagen type 1, and
d) providing constant flow of said osteogenic medium during the contacting step to produce a higher level of expression of at least one of said osteocalcin, said bone sialoprotein (bsp), said osteopontin (opn), and said collagen type 1 in said differentiated cells in the presence of said flowing of the osteogenic medium compared to in the absence of said flowing of the osteogenic medium.

2. The method of claim 1, wherein said seeding comprises seeding said MSCs on a first surface of said microfluidic device.
3. The method of claim 2, wherein said first surface comprises a porous flexible membrane, and wherein said membrane has a first surface and a second surface.
4. The method of claim 3, wherein said membrane is coated with extracellular matrix.
5. The method of claim 4, wherein said extracellular matrix comprises one or more of laminin, collagen, fibronectin, fibrin, vitronectin, hyaluronic acid, peptides, gelatin, decellularized bone marrow, and demineralized bone powder.
6. The method of claim 5, wherein said extracellular matrix comprises laminin.
7. The method of claim 3, wherein said membrane comprises endothelial cells attached to said second surface of said membrane.
8. The method of claim 2, wherein said first surface is coated with at least one extracellular matrix (ECM).
9. The method of claim 8, wherein said extracellular matrix comprises one or more of laminin, collagen, fibronectin, vitronectin, hyaluronic acid, peptides, gelatin, and decellularized bone marrow.
10. The method of claim 2, wherein said first surface is a surface of a first channel.
11. The method of claim 10, wherein said microfluidic device comprises endothelial cells attached to a second channel that is in fluidic communication with said first channel.
12. The method of claim 1, wherein said seeding comprises seeding said MSCs in a three-dimensional (3D) matrix.
13. The method of claim 12, wherein said 3D matrix comprises 3D gel.
14. The method of claim 12, wherein said 3D matrix comprises decellularized matrix.
15. The method of claim 12, wherein said 3D matrix comprises 3D extracellular matrix (ECM).
16. The method of claim 1, wherein said microfluidic device comprises a culture compartment, and said MSCs are comprised in said culture compartment.
17. The method of claim 16, wherein said culture compartment comprises an opening configured to provide direct access to one or more of said culture compartment and said MSCs.
18. The method of claim 1, further comprising applying mechanical stimulation to one or more of said MSCs, attached MSCs, proliferated attached MSCs, and differentiated cells.

* * * * *